US012751957B2

(12) United States Patent
Peng et al.

(10) Patent No.: US 12,751,957 B2
(45) Date of Patent: Oct. 6, 2026

(54) USE OF MULTIKINASE INHIBITOR

(71) Applicant: TransThera Sciences (Nanjing), Inc., Nanjing (CN)

(72) Inventors: Peng Peng, Nanjing (CN); Xiaoyan Qiang, Nanjing (CN); Frank Wu, Nanjing (CN)

(73) Assignee: TransThera Sciences (Nanjing), Inc., Nanjing (CN)

( * ) Notice: Subject to any disclaimer, the term of this patent is extended or adjusted under 35 U.S.C. 154(b) by 846 days.

(21) Appl. No.: 17/791,680

(22) PCT Filed: Feb. 23, 2021

(86) PCT No.: PCT/CN2021/077394

§ 371 (c)(1),
(2) Date: Jul. 8, 2022

(87) PCT Pub. No.: WO2021/169933

PCT Pub. Date: Sep. 2, 2021

(65) Prior Publication Data

US 2023/0129164 A1 Apr. 27, 2023

(30) Foreign Application Priority Data

Feb. 24, 2020 (CN) ........................ 202010112976.3

(51) Int. Cl.
*A61K 31/5517* (2006.01)
*A61P 35/00* (2006.01)

(52) U.S. Cl.
CPC .......... *A61K 31/5517* (2013.01); *A61P 35/00* (2018.01)

(58) Field of Classification Search
CPC ................................................ A61K 31/5517
See application file for complete search history.

(56) References Cited

U.S. PATENT DOCUMENTS

| | | | | |
|---|---|---|---|---|
| 10,208,042 B1 * | 2/2019 | Wu | | A61P 35/00 |
| 10,889,586 B2 | 1/2021 | Wu | | |
| 2015/0011536 A1 | 1/2015 | Wu et al. | | |
| 2016/0317499 A1 | 11/2016 | Nakanishi et al. | | |
| 2019/0040064 A1 | 2/2019 | Wu | | |
| 2021/0130354 A1 | 5/2021 | Wu | | |

FOREIGN PATENT DOCUMENTS

| | | | | |
|---|---|---|---|---|
| CA | 3100422 A1 | | 11/2019 | |
| CN | 102603743 A | | 7/2012 | |
| CN | 108218868 A | | 6/2018 | |
| WO | WO-2018108079 A1 | * | 6/2018 | C07D 47/14 |

OTHER PUBLICATIONS

Mahipal, Amit, et al. "FGFR2 genomic aberrations: Achilles heel in the management of advanced cholangiocarcinoma." Cancer treatment reviews 78 (2019): 1-7. (Year: 2019).*

Mahipal, Amit et al. "FGFR2 genomic aberrations: Achilles heel in the management of advanced cholangiocarcinoma." Cancer treatment reviews vol. 78 (2019): 1-7. doi: 10.1016/j.ctrv.2019.06.003 (Year: 2019).*

"FGFR2 genomic aberrations: Achilles heel in the management of advanced cholangiocarcinoma." Cancer treatment reviews 78 (2019): 1-7. (Year: 2019).*

Fang et al., PBA2 exhibits potent anti-tumor activity via suppression of VEGFR2 mediated-cell proliferation and angiogenesis. Biochem Pharmacol. Apr. 2018;150:131-140.

Liu et al., Antitumor activity of TY-011 against gastric cancer by inhibiting Aurora A, Aurora B and VEGFR2 kinases. J Exp Clin Cancer Res. Nov. 25, 2016;35(1):183, 15 pages.

International Search Report and Written Opinion for Application No. PCT/CN2021/077394, dated May 26, 2021, 10 pages.

Miao et al., Novel protein kinase inhibitor TT-00420 inhibits gallbladder cancer by inhibiting JNK/JUN-mediated signaling pathway. Cell Oncol (Dordr). Aug. 2022;45(4):689-708.

Peng et al., TT-00420, a dual mechanism kinase inhibitor targeting both mitosis and tumor microenvironment, is highly active against TNBC both in vitro and in vivo. Cancer Res. 2008;78(Suppl. 13):Abstract 5869, 4 pages.

STN Registry No. 2230490-29-4, Tinengotinib. 1 page, Jul. 11, 2018.

Wu, Trans Thera Biosciences Lead Product TT-00420 Granted Orphan Drug Designation from FDA to Treat Cholangiocarcinoma. Transthera Biosciences Press Release, 3 pages, Nov. 7, 2019.

* cited by examiner

*Primary Examiner* — Andrew D Kosar
*Assistant Examiner* — Connor K English
(74) *Attorney, Agent, or Firm* — McCarter & English, LLP; Wei Song

(57) ABSTRACT

The present invention belongs to the technical field of medicines, relates to novel use of a multi-kinase inhibitor, and particularly relates to a compound of general formula (I) or a pharmaceutically acceptable salt, a stereoisomer and a crystal form thereof for use in the treatment of biliary tract cancer, a pharmaceutical composition comprising the compound, a method for treating biliary tract cancer by using the compound, use of the compound in the treatment of biliary tract cancer, and use of the compound in the preparation of a medicament for treating biliary tract cancer. The variables in the general formula are defined in the specification. Research shows that the multi-kinase inhibitor compound of general formula (I) or the pharmaceutically acceptable salt, the stereoisomer and the crystal form thereof have a treatment effect on biliary tract cancer, and especially on cholangiocarcinoma, so that the compound of the present invention has huge clinical application potential.

(I)

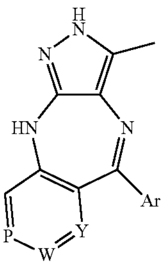

15 Claims, No Drawings

USE OF MULTIKINASE INHIBITOR

CROSS-REFERENCE TO RELATED APPLICATIONS

This application is a U.S. national stage filing, under 35 U.S.C. § 371 (c), of International Application No. PCT/CN2021/077394, filed on Feb. 23, 2021, which claims priority to Chinese Patent Application No. 202010112976.3, filed on Feb. 24, 2020.

TECHNICAL FIELD

The present invention belongs to the technical field of medicines, and particularly relates to a multi-kinase inhibitor compound or a pharmaceutically acceptable salt, a stereoisomer and a crystal form thereof for use in the treatment of biliary tract cancer, a pharmaceutical composition comprising the multi-kinase inhibitor compound or a pharmaceutically acceptable salt, a stereoisomer and a crystal form thereof, a method for treating biliary tract cancer by using the multi-kinase inhibitor compound or a pharmaceutically acceptable salt, a stereoisomer and a crystal form thereof, use of the multi-kinase inhibitor compound or a pharmaceutically acceptable salt, a stereoisomer and a crystal form thereof in the treatment of biliary tract cancer, and use of the multi-kinase inhibitor compound or a pharmaceutically acceptable salt, a stereoisomer and a crystal form thereof in the preparation of a medicament for treating biliary tract cancer.

BACKGROUND

Biliary tract cancer (BTC) is a malignant tumor derived from biliary epithelial cells, and is relatively rare clinically and has a low incidence rate, but in recent years, it tends to increase gradually. As its early clinical symptoms lack specificity, most diagnosed patients are at the advanced stage. It can be classified into cholangiocarcinoma (CCA) and gallbladder carcinoma (GBC) according to anatomical location.

Cholangiocarcinoma is a highly heterogeneous malignant tumor that develops in the biliary tract, accounting for approximately 3% of all digestive system tumors. Cholangiocarcinoma can be classified into three types according to the anatomical site of a lesion, including intrahepatic cholangiocarcinoma (iCC), perihilar cholangiocarcinoma (pCC), and distal cholangiocarcinoma (dCC). Intrahepatic cholangiocarcinoma is located in the liver parenchyma and accounts for approximately 10%-20% of cholangiocarcinoma, and perihilar cholangiocarcinoma and distal cholangiocarcinoma are both extrahepatic cholangiocarcinoma and accounts for approximately 80% of cholangiocarcinoma (Rizvi, S., & Gores, G. J. (2013), Pathogenesis, Diagnosis, and Management of Cholangiocarcinoma. Gastroenterology, 145(6), 1215-1229). The prognosis of cholangiocarcinoma is poor, wherein patients have no obvious clinical symptoms in the early stage, and metastasis usually occurs when diagnosis is confirmed. Because of the significant resistance of cholangiocarcinoma to chemotherapy, chemotherapy is often used in palliative treatments, the generally effective treatment being surgical resection and/or liver transplantation. Surgery is the primary treatment for resectable cholangiocarcinoma, and the post-operative survival rate depends mainly on tumor margin negativity, no vascular infiltration and lymphatic metastasis, and sufficient residual liver to be functional. Since most diagnosed patients are at the advanced stage, recurrence is common, with a recurrence rate of approximately 49%-64% within 2-3 years after surgical resection. The survival rate of patients after surgical resection for five years is also poor, with the survival rate of intrahepatic cholangiocarcinoma being 22%-44%, the survival rate of perihilar cholangiocarcinoma being 11%-41%, and the survival rate of distal cholangiocarcinoma being 27%-37%. Only less than ⅓ of patients have the opportunity to receive surgical resection due to local tumor infiltration, peritoneal or distant metastasis, lack of biliary reconstruction protocols, and prediction of insufficient residual liver after surgery. For cholangiocarcinoma patients who are unable to undergo surgical resection, another treatment option is liver transplantation. However, liver transplantation has very strict selection criteria and limited availability for patients, and even among patients who can receive liver transplantation, prognosis is still poor, the recurrence rate is high, and the survival rate is only 10%-25%. Currently, the preferred choice for treatment of patients with unresectable or metastatic tumors includes: 1) clinical trials; 2) fluorouracil-based or gemcitabine-based chemotherapy; or 3) optimal supportive treatment.

The incidence rate and mortality rate of cholangiocarcinoma is on an increasing trend year by year. Current research conditions suggest that the development and treatment of cholangiocarcinoma may be associated with multiple targets.

Fibroblast growth factor receptor (FGFR) can regulate the survival and proliferation of cells, and a plurality of researches suggest that FGFR aberration is a potential therapeutic target of a plurality of tumors. FGFR2 fusion is one of the important inducing factors of cholangiocarcinoma, and the gene is commonly found in intrahepatic cholangiocarcinoma and accounts for approximately 15% of intrahepatic cholangiocarcinoma. In addition to FGFR fusion aberration, cholangiocarcinoma has also been found to be drug resistant to a range of FGFR aberrations, such as FGFR2 N549H, FGFR2 V564F, FGFR3 K650E, and FGFR3 R248C (Shiao M S, Chiablaem K, Charoensawan V, et al. Emergence of Intrahepatic Cholangiocarcinoma: How High-Throughput Technologies Expedite the Solutions for a Rare Cancer Type. Frontiers in Genetics. 2018; 9:309).

The Janus kinase/signal transducer and activator of transcription (JAK/STAT) pathway may be involved in cancer cell proliferation and regulation of the tumor microenvironment via IL6 (Labib P L, Goodchild G, Pereira S P. Molecular Pathogenesis of Cholangiocarcinoma. BMC Cancer. 2019; 19(1):185). Constitutive phosphorylation of STATS has been reported in a panel of 7 different genetic profiles of human cholangiocarcinoma cell lines, demonstrating that the negative feedback loop of the IL-6/JAK/STAT3 pathway is epigenetically silenced in cholangiocarcinoma cells, resulting in sustained signaling (Isomoto H, Mott J L, Kobayashi S, et al. Sustained IL-6/STAT-3 signaling in cholangiocarcinoma cells due to SOCS-3 epigenetic silencing. Gastroenterology. 2007; 132(1):384-396).

The expression of Aurora A kinase (Aurora A) is also likely to be up-regulated in cholangiocarcinoma and is associated with poor progression-free survival and overall survival (Ding X, Huang T, Ahn K S, et al. Su 1459—Aurora Kinase A Sustains Cholangiocarcinoma Proliferation and Represents a New Therapeutic Target. Gastroenterology. 2018; 154(6):S-1153). WO2018108079A1 discloses a class of multi-kinase inhibitor compounds capable of inhibiting, modulating and/or regulating the activity of one or more protein kinases such as Aurora kinase and VEGFR kinase, thereby having an anti-tumor effect.

In summary, the optimal adjuvant therapy strategy after cholangiocarcinoma surgery is uncertain, and the clinical outcome in support of standard adjuvant therapy protocols is very limited. Currently, targeted inhibitors for cholangiocarcinoma are researched clinically, but there are still many cholangiocarcinoma patients who do not carry FGFR aberrations and also urgently need effective targeted therapy, so that huge unmet needs exist clinically for cholangiocarcinoma with FGFR aberration, non-FGFR aberration and wild type FGFR, and the research and development of effective targeted formulations for cholangiocarcinoma are urgently needed clinically.

SUMMARY

1. Brief Description of the Invention

The present invention researches novel use of a multi-kinase inhibitor compound of the following general formula (I) or a pharmaceutically acceptable salt, a stereoisomer and a crystal form thereof in the field of cancers. Researches find that the multi-kinase inhibitor compound of general formula (I) or the pharmaceutically acceptable salt, the stereoisomer and the crystal form thereof has a treatment effect on biliary tract cancer, and particularly has a remarkable treatment effect on cholangiocarcinoma.

Therefore, the present invention aims to provide novel use of a multi-kinase inhibitor compound of general formula (I) or a pharmaceutically acceptable salt, a stereoisomer and a crystal form thereof in the treatment of biliary tract cancer.

Therefore, in a first aspect of the present invention, provided is use of a compound of general formula (I) or a pharmaceutically acceptable salt, a stereoisomer and a crystal form thereof in the preparation of a medicament for treating biliary tract cancer:

(I)

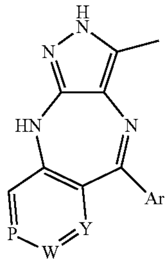

wherein Ar is phenyl optionally substituted with 1-3 $R_6$, each $R_6$ is independently selected from hydrogen, amino, cyano, halogen, $C_{1-4}$ alkyl and trifluoromethyl;

Y is $CR_3$;

P is $CR_4$;

W is N;

$R_3$ is selected from hydrogen and $C_{1-4}$ alkyl;

$R_4$ is $-(CH_2)_n-(5-11)$ membered heterocyclyl, wherein n=0-6, a ring-forming S atom in the heterocyclyl is optionally oxidized to S(O) or $S(O)_2$, a ring-forming C atom in the heterocyclyl is optionally oxidized to C(O), and the heterocyclyl is optionally substituted with one to more substituents independently selected from $C_{1-3}$ alkyl and $C_{3-6}$ cycloalkyl.

In a second aspect of the present invention, provided is use of a compound of general formula (I) or a pharmaceutically acceptable salt, a stereoisomer and a crystal form thereof in the treatment of biliary tract cancer:

(I)

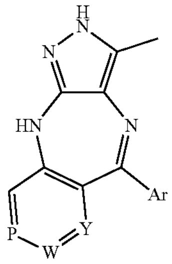

wherein the variables in the above general formula (I) are as defined above.

In a third aspect of the present invention, provided is a compound of general formula (I) or a pharmaceutically acceptable salt, a stereoisomer and a crystal form thereof for use in the treatment of biliary tract cancer:

(I)

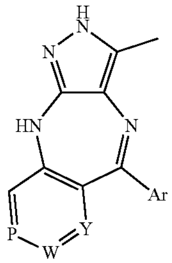

wherein the variables in the above general formula (I) are as defined above.

In a fourth aspect of the present invention, provided is a method for treating biliary tract cancer, comprising administering to a patient in need thereof a therapeutically effective amount of a compound of formula (I) or a pharmaceutically acceptable salt, a stereoisomer and a crystal form thereof:

(I)

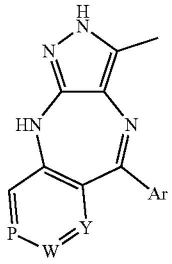

wherein the variables in the above general formula (I) are as defined above.

In a fifth aspect of the present invention, provided is a pharmaceutical composition for use in the treatment of biliary tract cancer, comprising a therapeutically effective amount of a compound of formula (I) or a pharmaceutically acceptable salt, a stereoisomer and a crystal form thereof, and optionally comprising a pharmaceutically acceptable carrier:

(I)

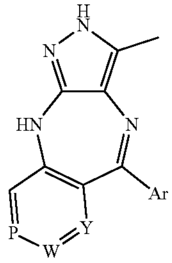

wherein the variables in the above general formula (I) are as defined above.

2. Detailed Description of the Invention

As described above, in the first aspect of the present invention, provided is use of a compound of general formula (I) or a pharmaceutically acceptable salt, a stereoisomer and a crystal form thereof in the preparation of a medicament for treating biliary tract cancer:

(I)

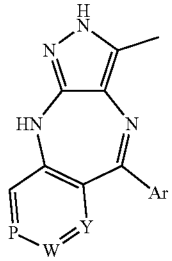

wherein the variables in the above general formula (I) are as defined above.

In one embodiment, Ar is phenyl optionally substituted with 1-3 $R_6$, and each $R_6$ is independently selected from hydrogen and halogen;

Y is $CR_3$;

P is $CR_4$;

W is N;

$R_3$ is hydrogen;

$R_4$ is selected from $-(CH_2)_n-$(5-6) membered monocyclic heterocyclyl and $-(CH_2)_n-$(7-11) membered fused heterocyclyl, wherein n=0-6, a ring-forming S atom in the heterocyclyl is optionally oxidized to S(O) or $S(O)_2$, a ring-forming C atom is optionally oxidized to C(O), and the heterocyclyl is optionally substituted with one to more substituents independently selected from $C_{1-3}$ alkyl and $C_{3-6}$ cycloalkyl.

In a further embodiment, the (5-6) membered monocyclic heterocyclyl is (5-6) membered saturated monocyclic heterocyclyl, and the (7-11) membered fused heterocyclyl is (7-11) membered saturated fused heterocyclyl. In a preferred embodiment, the (7-11) membered fused heterocyclyl is (7-11) membered saturated ortho-fused heterocyclyl, (7-11) membered saturated spiro-heterocyclyl or (7-11) membered saturated bridged heterocyclyl.

In one embodiment, the (5-11) membered heterocyclyl is

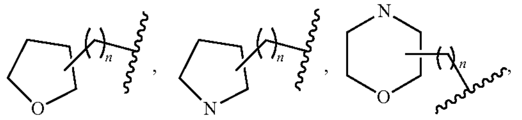
,
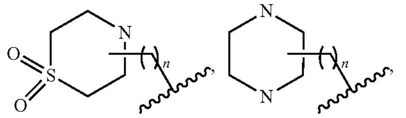
,
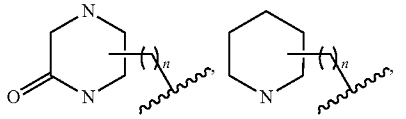
,
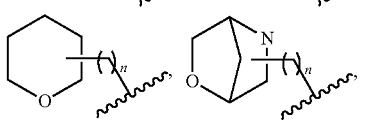
,
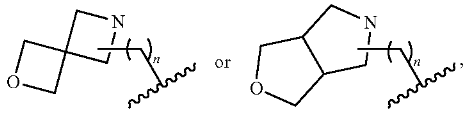
or and n=0-3, wherein the heterocyclyl is optionally substituted with one to more substituents independently selected from $C_{1-3}$ alkyl and $C_{3-6}$ cycloalkyl. In a preferred embodiment, the (5-11) membered heterocyclyl is

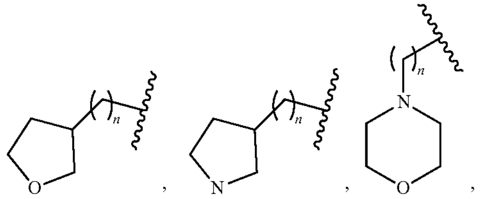
,
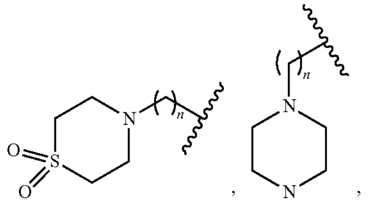
,
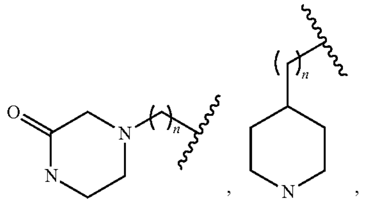
,
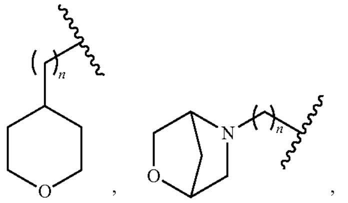
,
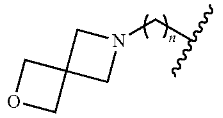

or

-continued

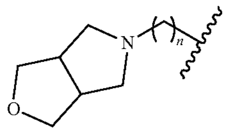

, and n=0-3, wherein the heterocyclyl is optionally substituted with one to more substituents independently selected from $C_{1-3}$ alkyl and $C_{3-6}$ cycloalkyl.

In one embodiment, the compound of general formula (I) is a compound shown in Table 1 or a pharmaceutically acceptable salt, a stereoisomer and a crystal form thereof.

TABLE 1

Compounds of the present invention

| No. | Structure | No. | Structure |
|---|---|---|---|
| 1 | 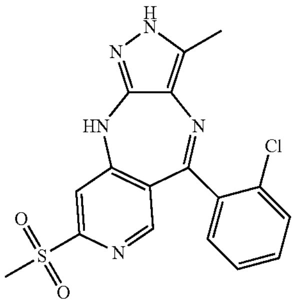 [SMILES: Cc1[nH]nc2c1N=C(c1ccccc1Cl)c1cnc(S(C)(=O)=O)cc1N2] | 2 | 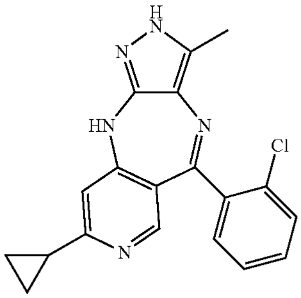 |
| 3 | 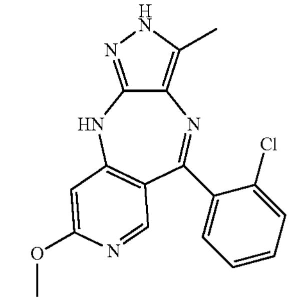 [SMILES: COc1cc2c(cn1)C(c1ccccc1Cl)=Nc1c(n[nH]c1C)N2] | 4 | 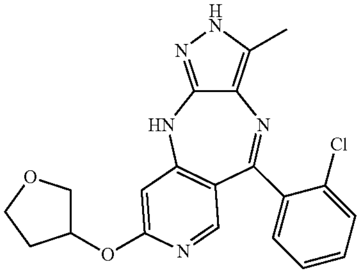 [SMILES: Cc1[nH]nc2c1N=C(c1ccccc1Cl)c1cnc(OC3CCOC3)cc1N2] |
| 5 | 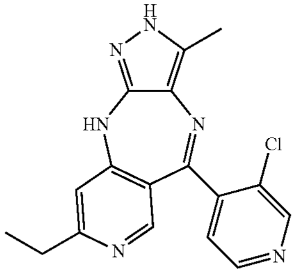 [SMILES: CCc1cc2c(cn1)C(c1ccncc1Cl)=Nc1c(n[nH]c1C)N2] | 6 | 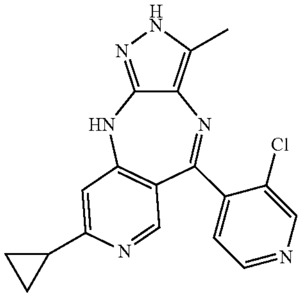 |
| 7 | 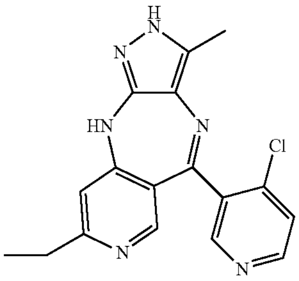 [SMILES: CCc1cc2c(cn1)C(c1cnccc1Cl)=Nc1c(n[nH]c1C)N2] | 8 | 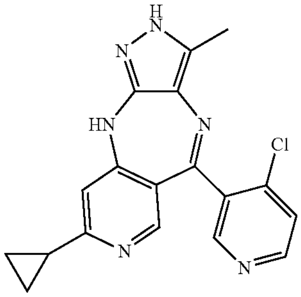 [SMILES: Cc1[nH]nc2c1N=C(c1cnccc1Cl)c1cnc(C3CC3)cc1N2] |

TABLE 1-continued
| Compounds of the present invention | | | |
|---|---|---|---|
| No. | Structure | No. | Structure |
| 9 | 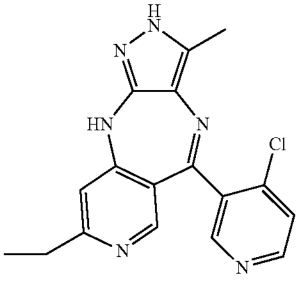 [SMILES: CCc1cc2c(cn1)C(c1cnccc1Cl)=Nc1c(n[nH]c1C)N2] | 10 | 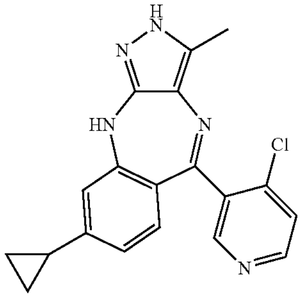 [SMILES: Cc1[nH]nc2c1N=C(c1cnccc1Cl)c1ccc(C3CC3)cc1N2] |
| 11 | 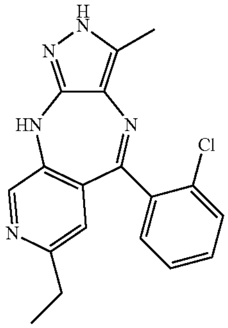 [SMILES: CCc1cc2c(cn1)Nc1n[nH]c(C)c1N=C2c1ccccc1Cl] | 12 | 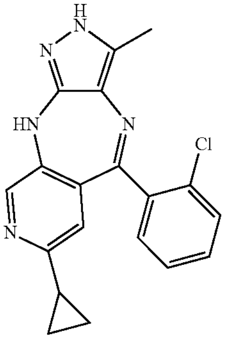 [SMILES: Cc1[nH]nc2c1N=C(c1ccccc1Cl)c1cc(C3CC3)ncc1N2] |
| 13 | 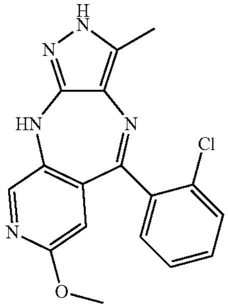 [SMILES: COc1cc2c(cn1)Nc1n[nH]c(C)c1N=C2c1ccccc1Cl] | 14 | 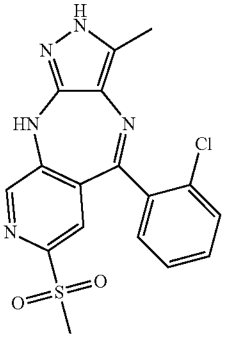 [SMILES: Cc1[nH]nc2c1N=C(c1ccccc1Cl)c1cc(S(C)(=O)=O)ncc1N2] |
| 15 | 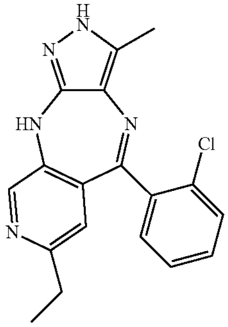 [SMILES: CCc1cc2c(cn1)Nc1n[nH]c(C)c1N=C2c1ccccc1Cl] | 16 | 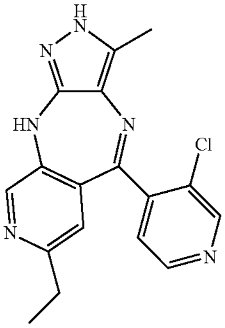 [SMILES: CCc1cc2c(cn1)Nc1n[nH]c(C)c1N=C2c1ccncc1Cl] |

TABLE 1-continued
| Compounds of the present invention | | | |
|---|---|---|---|
| No. | Structure | No. | Structure |
| 17 | 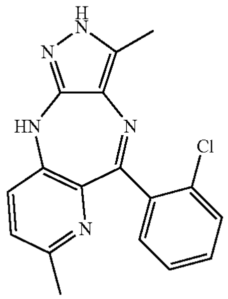 [SMILES: Cc1ccc2c(n1)C(c1ccccc1Cl)=Nc1c(n[nH]c1C)N2] | 18 | 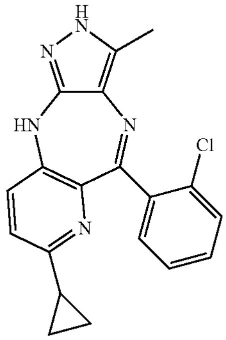 [SMILES: Cc1[nH]nc2c1N=C(c1ccccc1Cl)c1nc(C3CC3)ccc1N2] |
| 19 | 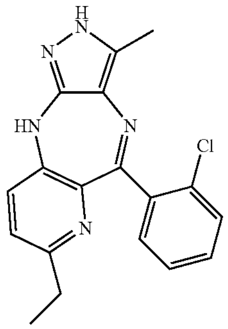 [SMILES: CCc1ccc2c(n1)C(c1ccccc1Cl)=Nc1c(n[nH]c1C)N2] | 20 | 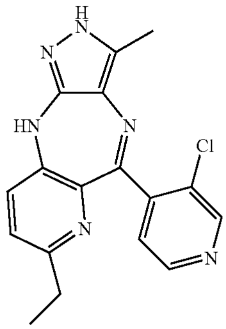 [SMILES: CCc1ccc2c(n1)C(c1ccncc1Cl)=Nc1c(n[nH]c1C)N2] |
| 21 | 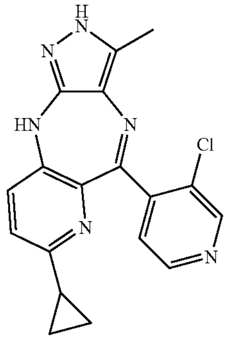 [SMILES: Cc1[nH]nc2c1N=C(c1ccncc1Cl)c1nc(C3CC3)ccc1N2] | 22 | 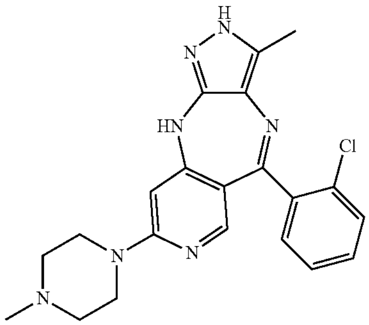 [SMILES: Cc1[nH]nc2c1N=C(c1ccccc1Cl)c1cnc(N3CCN(C)CC3)cc1N2] |
| 23 | 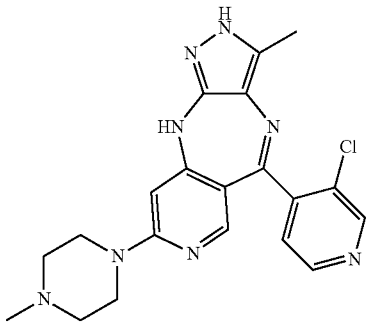 [SMILES: Cc1[nH]nc2c1N=C(c1ccncc1Cl)c1cnc(N3CCN(C)CC3)cc1N2] | 24 | 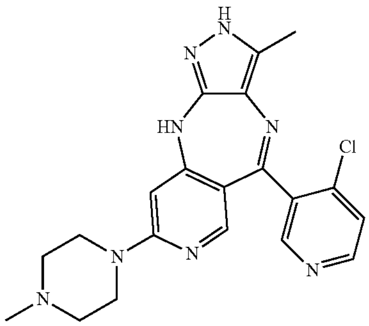 |

TABLE 1-continued
| Compounds of the present invention | | | |
|---|---|---|---|
| No. | Structure | No. | Structure |
| 25 | 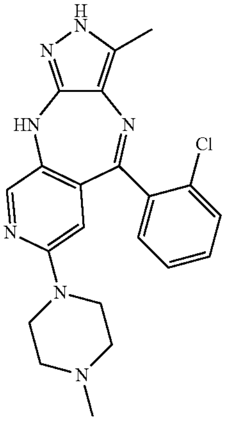 [SMILES: Cc1[nH]nc2c1N=C(c1ccccc1Cl)c1cc(N3CCN(C)CC3)ncc1N2] | 26 | 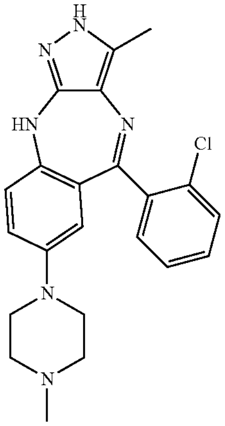 [SMILES: Cc1[nH]nc2c1N=C(c1ccccc1Cl)c1cc(N3CCN(C)CC3)ccc1N2] |
| 27 | 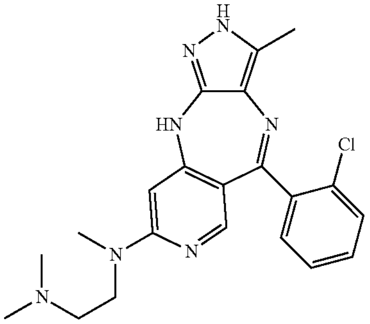 [SMILES: Cc1[nH]nc2c1N=C(c1ccccc1Cl)c1cnc(N(C)CCN(C)C)cc1N2] | 28 | 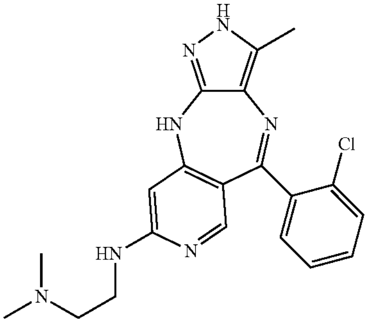 [SMILES: Cc1[nH]nc2c1N=C(c1ccccc1Cl)c1cnc(NCCN(C)C)cc1N2] |
| 29 | 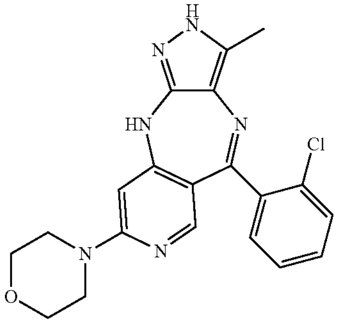 [SMILES: Cc1[nH]nc2c1N=C(c1ccccc1Cl)c1cnc(N3CCOCC3)cc1N2] | 30 | 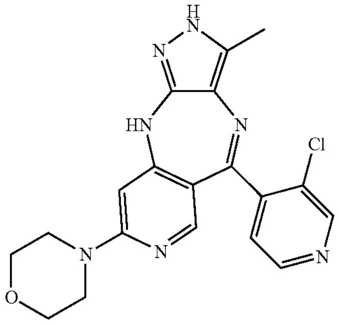 [SMILES: Cc1[nH]nc2c1N=C(c1ccncc1Cl)c1cnc(N3CCOCC3)cc1N2] |
| 31 | 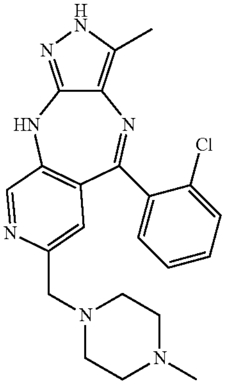 [SMILES: Cc1[nH]nc2c1N=C(c1ccccc1Cl)c1cc(CN3CCN(C)CC3)ncc1N2] | 32 | 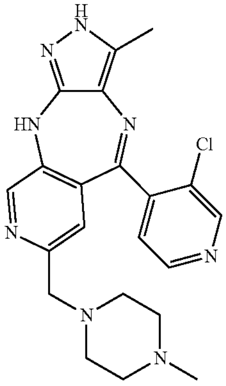 [SMILES: Cc1[nH]nc2c1N=C(c1ccncc1Cl)c1cc(CN3CCN(C)CC3)ncc1N2] |

TABLE 1-continued
| Compounds of the present invention | | | |
|---|---|---|---|
| No. | Structure | No. | Structure |
| 33 | 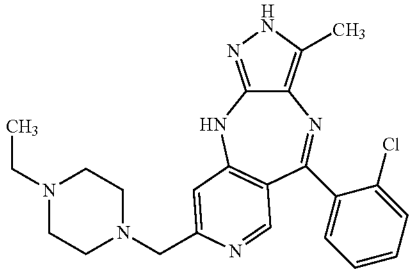 [SMILES: CCN1CCN(Cc2cc3c(cn2)C(c2ccccc2Cl)=Nc2c(n[nH]c2C)N3)CC1] | 34 | 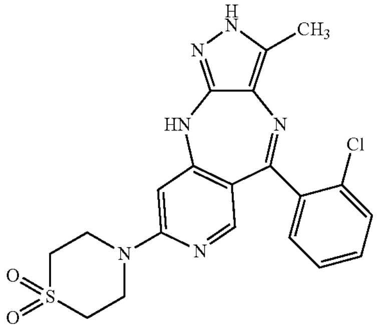 [SMILES: Cc1[nH]nc2c1N=C(c1ccccc1Cl)c1cnc(N3CCS(=O)(=O)CC3)cc1N2] |
| 35 | 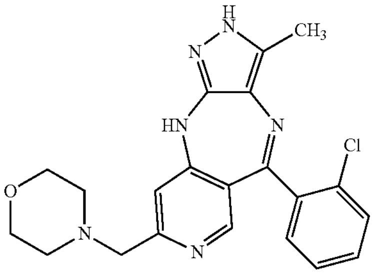 [SMILES: Cc1[nH]nc2c1N=C(c1ccccc1Cl)c1cnc(CN3CCOCC3)cc1N2] | 36 | 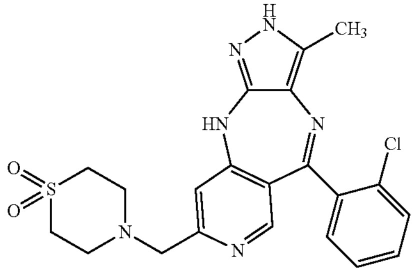 [SMILES: Cc1[nH]nc2c1N=C(c1ccccc1Cl)c1cnc(CN3CCS(=O)(=O)CC3)cc1N2] |
| 37 | 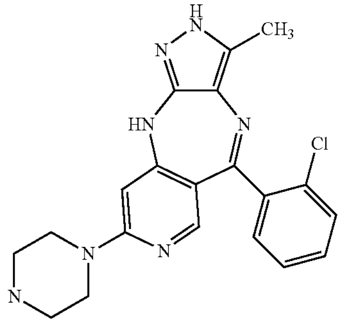 [SMILES: Cc1[nH]nc2c1N=C(c1ccccc1Cl)c1cnc(N3CCNCC3)cc1N2] | 38 | 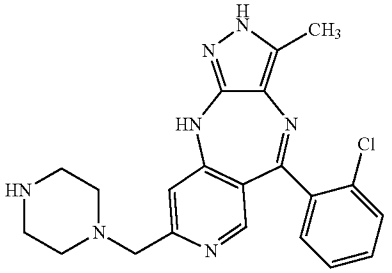 [SMILES: Cc1[nH]nc2c1N=C(c1ccccc1Cl)c1cnc(CN3CCNCC3)cc1N2] |
| 39 | 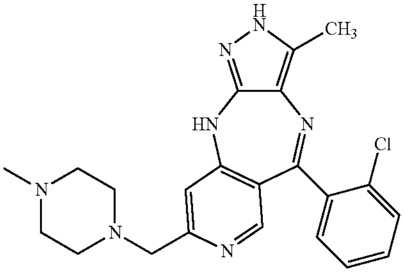 [SMILES: Cc1[nH]nc2c1N=C(c1ccccc1Cl)c1cnc(CN3CCN(C)CC3)cc1N2] | 40 | 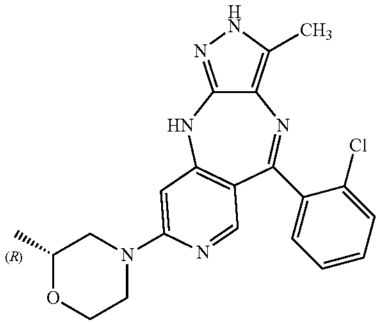 |

TABLE 1-continued
Compounds of the present invention
| No. | Structure | No. | Structure |
|---|---|---|---|
| 41 | 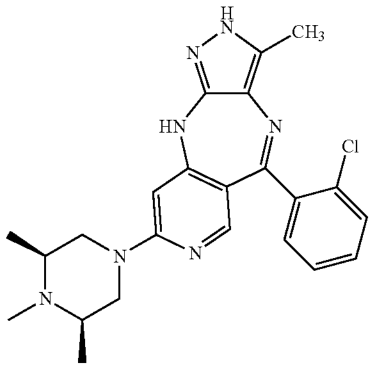 [SMILES: Cc1[nH]nc2c1N=C(c1ccccc1Cl)c1cnc(N3C[C@@H](C)N(C)[C@@H](C)C3)cc1N2] | 42 | 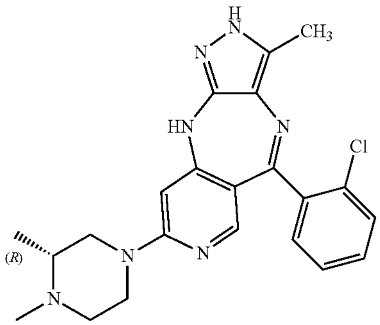 |
| 43 | 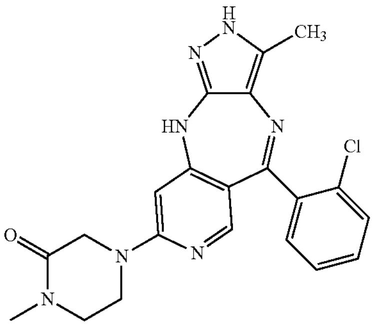 [SMILES: Cc1[nH]nc2c1N=C(c1ccccc1Cl)c1cnc(N3CCN(C)C(=O)C3)cc1N2] | 44 | 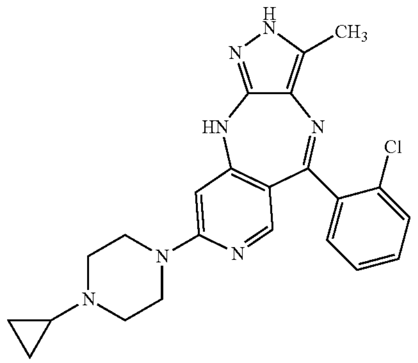 [SMILES: Cc1[nH]nc2c1N=C(c1ccccc1Cl)c1cnc(N3CCN(C4CC4)CC3)cc1N2] |
| 45 | 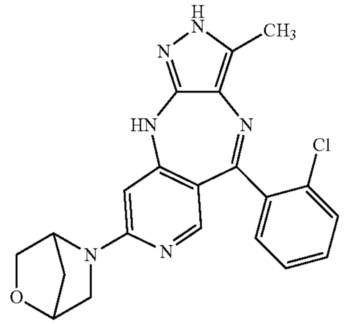 [SMILES: Cc1[nH]nc2c1N=C(c1ccccc1Cl)c1cnc(N3CC4CC3CO4)cc1N2] | 46 | 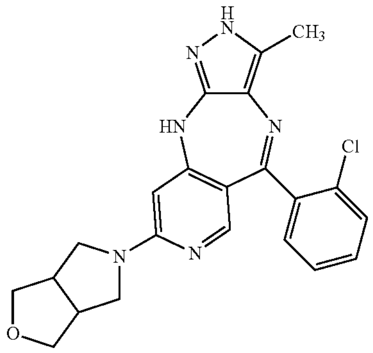 [SMILES: Cc1[nH]nc2c1N=C(c1ccccc1Cl)c1cnc(N3CC4COCC4C3)cc1N2] |
| 47 | 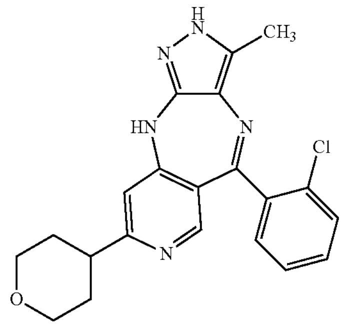 [SMILES: Cc1[nH]nc2c1N=C(c1ccccc1Cl)c1cnc(C3CCOCC3)cc1N2] | 48 | 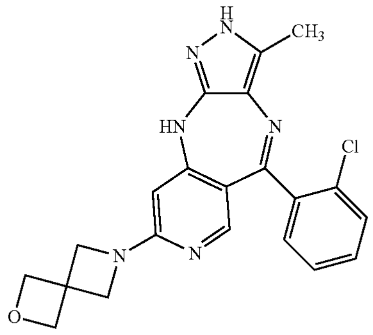 [SMILES: Cc1[nH]nc2c1N=C(c1ccccc1Cl)c1cnc(N3CC4(COC4)C3)cc1N2] |

TABLE 1-continued

| Compounds of the present invention | | | |
|---|---|---|---|
| No. | Structure | No. | Structure |
| 49 | 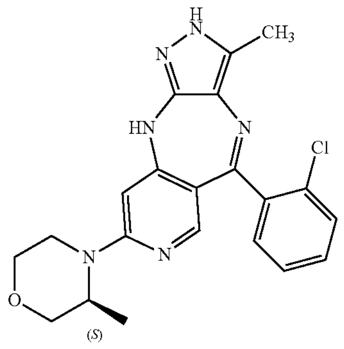 | 50 | 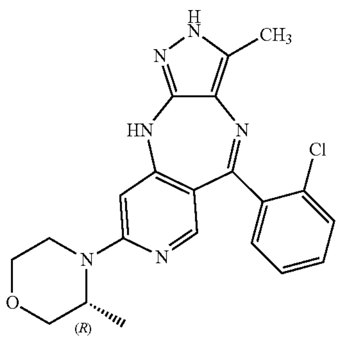 |
| 51 | 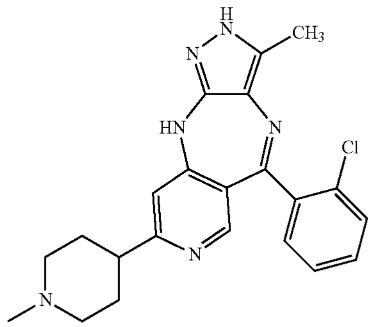 [SMILES: Cc1[nH]nc2c1N=C(c1ccccc1Cl)c1cnc(C3CCN(C)CC3)cc1N2] | | |

In a preferred embodiment, the compound of general formula (I) is

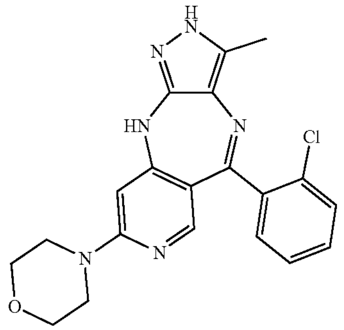

or a pharmaceutically acceptable salt, a stereoisomer and a crystal form thereof.

In one embodiment, the biliary tract cancer refers to cholangiocarcinoma.

In a further embodiment, the cholangiocarcinoma refers to an FGFR-mediated cholangiocarcinoma. In a preferred embodiment, the FGFR-mediated cholangiocarcinoma refers to cholangiocarcinoma mediated by any one of FGFR1, FGFR2 and FGFR3 or any combination thereof.

In another further embodiment, the cholangiocarcinoma refers to a cholangiocarcinoma with non-FGFR aberration. In a preferred embodiment, the cholangiocarcinoma with non-FGFR aberration refers to cholangiocarcinoma with non-FGFR2 aberration.

In another further embodiment, the cholangiocarcinoma refers to a cholangiocarcinoma with FGFR aberration cholangiocarcinoma. In a preferred embodiment, the cholangiocarcinoma with FGFR aberration refers to a cholangiocarcinoma with FGFR2 and/or FGFR3 aberration.

In still further embodiments, the cholangiocarcinoma refers to cholangiocarcinoma with any one of FGFR fusion, FGFR mutation and FGFR overexpression or any combination thereof. Wherein the FGFR mutation comprises an FGFR point mutation and an FGFR insertion/deletion mutation.

In a preferred embodiment, the cholangiocarcinoma refers to cholangiocarcinoma with any one of FGFR2 fusion, FGFR2 and/or FGFR3 mutation and FGFR overexpression or any combination thereof. In another preferred embodiment, the cholangiocarcinoma refers to cholangiocarcinoma with FGFR2 fusion. In another preferred embodiment, the cholangiocarcinoma refers to cholangiocarcinoma with FGFR2 and/or FGFR3 mutation. In another preferred embodiment, the cholangiocarcinoma refers to cholangiocarcinoma with any one of FGFR2 N549H, FGFR2 V564F and FGFR3 K650E or any combination thereof.

In another further embodiment, the cholangiocarcinoma refers to drug-resistant cholangiocarcinoma that is positive for FGFR aberration but not responsive to an FGFR inhibitor, or drug-resistant cholangiocarcinoma after administration of an FGFR inhibitor. In a preferred embodiment, the cholangiocarcinoma refers to a drug-resistant cholangiocarcinoma with FGFR2 and/or FGFR3 aberration.

In another further embodiment, the cholangiocarcinoma refers to any one of intrahepatic cholangiocarcinoma, perihilar cholangiocarcinoma and distal cholangiocarcinoma or any combination thereof. In a preferred embodiment, the cholangiocarcinoma refers to perihilar cholangiocarcinoma. In a preferred embodiment, the cholangiocarcinoma refers to distal cholangiocarcinoma. In a preferred embodiment, the cholangiocarcinoma refers to intrahepatic cholangiocarcinoma. In another preferred embodiment, the intrahepatic cholangiocarcinoma refers to intrahepatic cholangiocarcinoma with FGFR2 aberration. In another preferred embodiment, the intrahepatic cholangiocarcinoma refers to intrahepatic cholangiocarcinoma with FGFR2 fusion. In another preferred embodiment, the intrahepatic cholangiocarcinoma refers to intrahepatic cholangiocarcinoma with non-FGFR aberration.

In one embodiment, the cholangiocarcinoma further comprises cholangiocarcinoma mediated by other mechanisms, including Aurora-kinase-mediated cholangiocarcinoma and cholangiocarcinoma caused by abnormal IL-6-mediated JAK-STAT signaling pathway.

In one embodiment, the medicament for treating biliary tract cancer may further comprise a pharmaceutically acceptable carrier in addition to the compound of general formula (I) or the pharmaceutically acceptable salt, the stereoisomer and the crystal form thereof.

In one embodiment, the medicament may comprise one or more pharmaceutically acceptable carriers, and may be administered to a patient or subject in need of such treatment by oral, parenteral, rectal, or transpulmonary administration, and the like. For oral administration, the pharmaceutical composition can be prepared into a conventional solid formulation, such as tablets, capsules, pills and granules; or can be prepared into an oral liquid formulation, such as oral solutions, oral suspensions and syrups. In the preparation of an oral formulation, an appropriate filler, binder, disintegrant, lubricant and the like may be added. For parenteral administration, the pharmaceutical composition can be prepared into an injection, including a solution injection, a sterile powder for injection and a concentrated solution for injection. The injection can be produced by a conventional method existing in the pharmaceutical field, and during the preparation process, no additive may be added, or an appropriate additive may be added according to the property of the medicament. For rectal administration, the pharmaceutical composition can be prepared into a suppository and the like. For transpulmonary administration, the pharmaceutical composition can be prepared into an inhalant, a spray or the like.

In one embodiment, the medicament for treating biliary tract cancer further comprises one or more second therapeutically active agents in addition to the compound of general formula (I) or the pharmaceutically acceptable salt, the stereoisomer and the crystal form thereof.

In a further embodiment, the second therapeutically active agent is an antimetabolite, a growth factor inhibitor, a mitotic inhibitor, an anti-tumor hormone, an alkylating agent, metallic platinum, a topoisomerase inhibitor, a hormonal drug, an immunomodulator, a tumor suppressor gene, a cancer vaccine, or an immune checkpoint inhibitor.

In one embodiment, the compound of general formula (I) or the pharmaceutically acceptable salt, the stereoisomer and the crystal form thereof and the second therapeutically active agent are administered to a patient or subject in need of treatment in combination.

In one embodiment, the compound of general formula (I) or the pharmaceutically acceptable salt, the stereoisomer and the crystal form thereof and the second therapeutically active agent are administered to a patient or subject in need of treatment sequentially, simultaneously or in a combined formulation.

In a further embodiment, the patient or subject is a mammal. In a preferred embodiment, the patient or subject is a human.

In a second aspect of the present invention, provided is a compound of general formula (I) or a pharmaceutically acceptable salt, a stereoisomer and a crystal form thereof for use in the treatment of biliary tract cancer, (I)

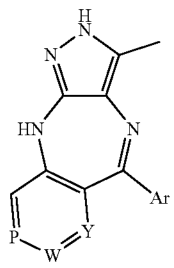

wherein the variables in the above general formula (I) are as defined above.

In one embodiment, Ar is phenyl optionally substituted with 1-3 $R_6$, and each $R_6$ is independently selected from hydrogen and halogen;

Y is $CR_3$;

P is $CR_4$;

W is N;

$R_3$ is hydrogen;

$R_4$ is selected from $-(CH_2)_n$-(5-6) membered monocyclic heterocyclyl and $-(CH_2)_n$-(7-11) membered fused heterocyclyl, wherein n=0-6, a ring-forming S atom in the heterocyclyl is optionally oxidized to S(O) or $S(O)_2$, a ring-forming C atom is optionally oxidized to C(O), and the heterocyclyl is optionally substituted with one to more substituents independently selected from $C_{1-3}$ alkyl and $C_{3-6}$ cycloalkyl.

In a further embodiment, the (5-6) membered monocyclic heterocyclyl is (5-6) membered saturated monocyclic heterocyclyl, and the (7-11) membered fused heterocyclyl is (7-11) membered saturated fused heterocyclyl. In a preferred embodiment, the (7-11) membered fused heterocyclyl is (7-11) membered saturated ortho-fused heterocyclyl, (7-11) membered saturated spiro-heterocyclyl or (7-11) membered saturated bridged heterocyclyl.

In one embodiment, the (5-11) membered heterocyclyl is

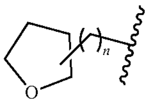 , 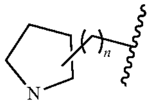 ,

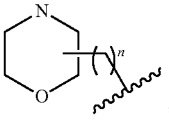 , 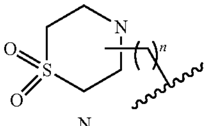 ,

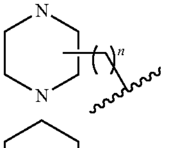 , 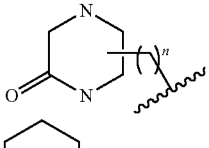 ,

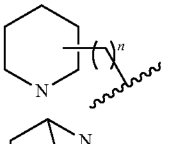 , 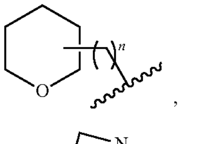 ,

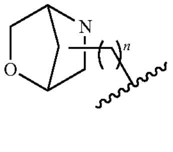 , 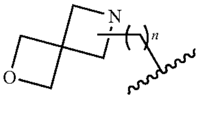 or

-continued

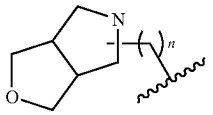, and n=0-3, wherein the heterocyclyl is optionally substituted with one to more substituents independently selected from $C_{1-3}$ alkyl and $C_{3-6}$ cycloalkyl. In a preferred embodiment, the (5-11) membered heterocyclyl is

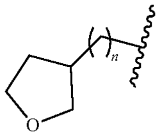, 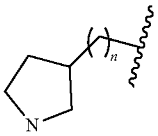, 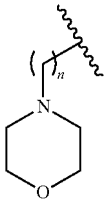, 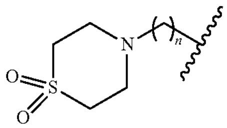, 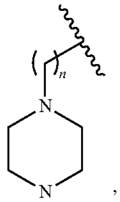, 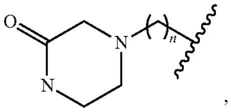, 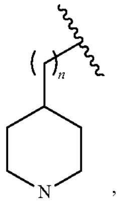, 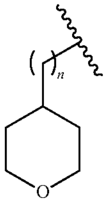, 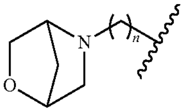, 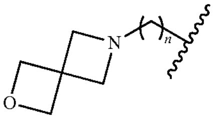 or 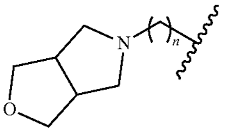, and n=0-3, wherein the heterocyclyl is optionally substituted with one to more substituents independently selected from $C_{1-3}$ alkyl and $C_{3-6}$ cycloalkyl.

In one embodiment, the compound of general formula (I) is a compound shown in Table 1 or a pharmaceutically acceptable salt, a stereoisomer and a crystal form thereof.

In a preferred embodiment, the compound of general formula (I) is

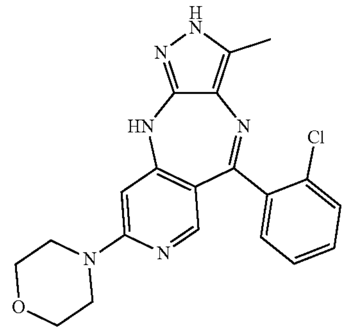

or a pharmaceutically acceptable salt, a stereoisomer and a crystal form thereof.

In one embodiment, the biliary tract cancer refers to cholangiocarcinoma.

In a further embodiment, the cholangiocarcinoma refers to an FGFR-mediated cholangiocarcinoma. In a preferred embodiment, the FGFR-mediated cholangiocarcinoma refers to cholangiocarcinoma mediated by any one of FGFR1, FGFR2 and FGFR3 or any combination thereof.

In another further embodiment, the cholangiocarcinoma refers to a cholangiocarcinoma with non-FGFR aberration. In a preferred embodiment, the cholangiocarcinoma with non-FGFR aberration refers to cholangiocarcinoma with non-FGFR2 aberration.

In another further embodiment, the cholangiocarcinoma refers to a cholangiocarcinoma with FGFR aberration. In a preferred embodiment, the cholangiocarcinoma with FGFR aberration refers to a cholangiocarcinoma with FGFR2 and/or FGFR3 aberration.

In still further embodiments, the cholangiocarcinoma refers to cholangiocarcinoma with any one of FGFR fusion, FGFR mutation and FGFR overexpression or any combination thereof. Wherein the FGFR mutation comprises an FGFR point mutation and an FGFR insertion/deletion mutation.

In a preferred embodiment, the cholangiocarcinoma refers to cholangiocarcinoma with any one of FGFR2 fusion, FGFR2 and/or FGFR3 mutation and FGFR overexpression or any combination thereof. In another preferred embodiment, the cholangiocarcinoma refers to cholangiocarcinoma with FGFR2 fusion. In another preferred embodiment, the cholangiocarcinoma refers to cholangiocarcinoma with FGFR2 and/or FGFR3 mutation. In another preferred embodiment, the cholangiocarcinoma refers to cholangiocarcinoma with any one of FGFR2 N549H, FGFR2 V564F and FGFR3 K650E or any combination thereof.

In another further embodiment, the cholangiocarcinoma refers to drug-resistant cholangiocarcinoma that is positive for FGFR aberration but not responsive to an FGFR inhibitor, or drug-resistant cholangiocarcinoma after administration of an FGFR inhibitor. In a preferred embodiment, the cholangiocarcinoma refers to drug-resistant cholangiocarcinoma with FGFR2 and/or FGFR3 aberration.

In another further embodiment, the cholangiocarcinoma refers to any one of intrahepatic cholangiocarcinoma, perihilar cholangiocarcinoma and distal cholangiocarcinoma or any combination thereof. In a preferred embodiment, the cholangiocarcinoma refers to perihilar cholangiocarcinoma. In a preferred embodiment, the cholangiocarcinoma refers to distal cholangiocarcinoma. In a preferred embodiment, the cholangiocarcinoma refers to intrahepatic cholangiocarcinoma. In another preferred embodiment, the intrahepatic cholangiocarcinoma refers to intrahepatic cholangiocarcinoma with FGFR2 aberration. In another preferred embodiment, the intrahepatic cholangiocarcinoma refers to intrahepatic cholangiocarcinoma with FGFR2 fusion. In another preferred embodiment, the intrahepatic cholangiocarcinoma refers to intrahepatic cholangiocarcinoma with non-FGFR aberration.

In one embodiment, the cholangiocarcinoma further comprises cholangiocarcinoma mediated by other mechanisms, including Aurora-kinase-mediated cholangiocarcinoma and cholangiocarcinoma caused by abnormal IL-6-mediated JAK-STAT signaling pathway.

In one embodiment, the use comprises administering to a patient or subject in need thereof a therapeutically effective amount of a compound of general formula (I) or a pharmaceutically acceptable salt, a stereoisomer and a crystal form thereof.

In one embodiment, a therapeutically effective amount of the compound of general formula (I) or the pharmaceutically acceptable salt, the stereoisomer and the crystal form thereof may be further prepared with one or more pharmaceutically acceptable carriers into any pharmaceutically acceptable pharmaceutical formulation.

In one embodiment, the pharmaceutical formulation may comprise one or more pharmaceutically acceptable carriers, and may be administered to a patient or subject in need of such treatment by oral, parenteral, rectal, or transpulmonary administration, and the like. For oral administration, the pharmaceutical composition can be prepared into a conventional solid formulation, such as tablets, capsules, pills and granules; or can be prepared into an oral liquid formulation, such as oral solutions, oral suspensions and syrups. In the preparation of an oral formulation, an appropriate filler, binder, disintegrant, lubricant and the like may be added. For parenteral administration, the pharmaceutical composition can be prepared into an injection, including a solution injection, a sterile powder for injection and a concentrated solution for injection. The injection can be produced by a conventional method existing in the pharmaceutical field, and during the preparation process, no additive may be added, or an appropriate additive may be added according to the property of the medicament. For rectal administration, the pharmaceutical composition can be prepared into a suppository and the like. For transpulmonary administration, the pharmaceutical composition can be prepared into an inhalant, a spray or the like.

In one embodiment, the use further comprises administering to a patient or subject in need thereof a therapeutically effective amount of a compound of general formula (I) or a pharmaceutically acceptable salt, a stereoisomer and a crystal form thereof and one or more second therapeutically active agents.

In a further embodiment, the second therapeutically active agent is an antimetabolite, a growth factor inhibitor, a mitotic inhibitor, an anti-tumor hormone, an alkylating agent, metallic platinum, a topoisomerase inhibitor, a hormonal drug, an immunomodulator, a tumor suppressor gene, a cancer vaccine, or an immune checkpoint inhibitor.

In one embodiment, the compound of general formula (I) or the pharmaceutically acceptable salt, the stereoisomer and the crystal form thereof and the second therapeutically active agent are administered to a patient or subject in need of treatment in combination.

In one embodiment, the compound of general formula (I) or the pharmaceutically acceptable salt, the stereoisomer and the crystal form thereof and the second therapeutically active agent are administered to a patient or subject in need of treatment sequentially, simultaneously or in a combined formulation.

In a further embodiment, the patient or subject is a mammal. In a preferred embodiment, the patient or subject is a human.

In a third aspect of the present invention, provided is a compound of general formula (I) or a pharmaceutically acceptable salt, a stereoisomer and a crystal form thereof for use in the treatment of biliary tract cancer:

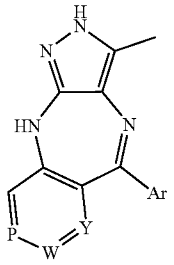

(I)

wherein the variables in the above general formula (I) are as defined above.

In one embodiment, Ar is phenyl optionally substituted with 1-3 $R_6$, and each $R_6$ is independently selected from hydrogen and halogen;

Y is $CR_3$;

P is $CR_4$;

W is N;

$R_3$ is hydrogen;

$R_4$ is selected from $-(CH_2)_n$-(5-6) membered monocyclic heterocyclyl and $-(CH_2)_n$-(7-11) membered fused heterocyclyl, wherein n=0-6, a ring-forming S atom in the heterocyclyl is optionally oxidized to S(O) or $S(O)_2$, a ring-forming C atom is optionally oxidized to C(O), and the heterocyclyl is optionally substituted with one to more substituents independently selected from $C_{1-3}$ alkyl and $C_{3-6}$ cycloalkyl.

In a further embodiment, the (5-6) membered monocyclic heterocyclyl is (5-6) membered saturated monocyclic heterocyclyl, and the (7-11) membered fused heterocyclyl is (7-11) membered saturated fused heterocyclyl. In a preferred embodiment, the (7-11) membered fused heterocyclyl is (7-11) membered saturated ortho-fused heterocyclyl, (7-11) membered saturated spiro-heterocyclyl or (7-11) membered saturated bridged heterocyclyl.

In one embodiment, the (5-11) membered heterocyclyl is

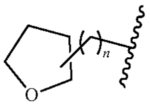 , 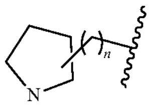 ,

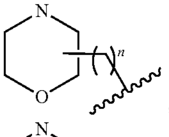 , 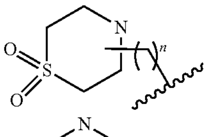 ,

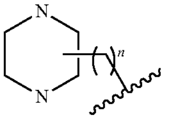 , 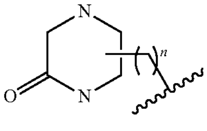 ,

-continued

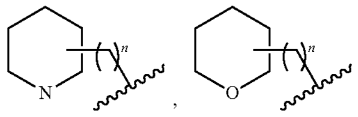

, ,

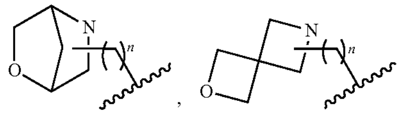

, or

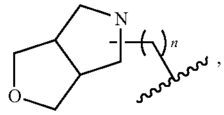

, and n=0-3, wherein the heterocyclyl is optionally substituted with one to more substituents independently selected from $C_{1-3}$ alkyl and $C_{3-6}$ cycloalkyl. In a preferred embodiment, the (5-11) membered heterocyclyl is

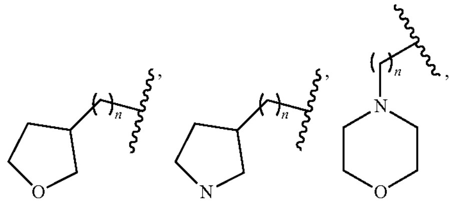

, , ,

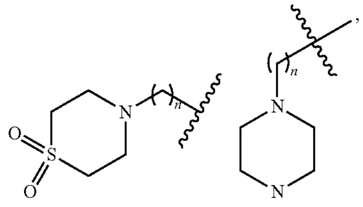

, ,

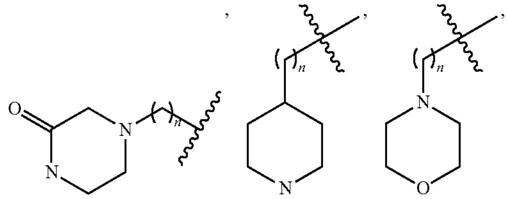

, , ,

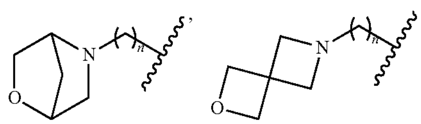

, or

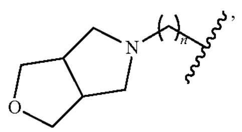

, and n=0-3, wherein the heterocyclyl is optionally substituted with one to more substituents independently selected from $C_{1-3}$ alkyl and $C_{3-6}$ cycloalkyl.

In one embodiment, the compound of general formula (I) is a compound shown in Table 1 or a pharmaceutically acceptable salt, a stereoisomer and a crystal form thereof.

In a preferred embodiment, the compound of general formula (I) is

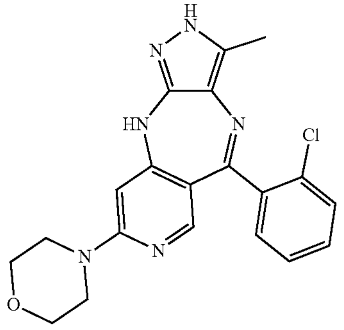

or a pharmaceutically acceptable salt, a stereoisomer and a crystal form thereof.

In one embodiment, the biliary tract cancer refers to cholangiocarcinoma.

In a further embodiment, the cholangiocarcinoma refers to an FGFR-mediated cholangiocarcinoma. In a preferred embodiment, the FGFR-mediated cholangiocarcinoma refers to cholangiocarcinoma mediated by any one of FGFR1, FGFR2 and FGFR3 or any combination thereof.

In another further embodiment, the cholangiocarcinoma refers to a cholangiocarcinoma with non-FGFR aberration. In a preferred embodiment, the cholangiocarcinoma with non-FGFR aberration refers to a cholangiocarcinoma with non-FGFR2 aberration.

In another further embodiment, the cholangiocarcinoma refers to a cholangiocarcinoma with FGFR aberration. In a preferred embodiment, the cholangiocarcinoma with FGFR aberration refers to a cholangiocarcinoma with FGFR2 and/or FGFR3 aberration.

In still further embodiments, the cholangiocarcinoma refers to cholangiocarcinoma with any one of FGFR fusion, FGFR mutation and FGFR overexpression or any combination thereof. Wherein the FGFR mutation comprises an FGFR point mutation and an FGFR insertion/deletion mutation.

In a preferred embodiment, the cholangiocarcinoma refers to cholangiocarcinoma with any one of FGFR2 fusion, FGFR2 and/or FGFR3 mutation and FGFR overexpression or any combination thereof. In another preferred embodiment, the cholangiocarcinoma refers to cholangiocarcinoma with FGFR2 fusion. In another preferred embodiment, the cholangiocarcinoma refers to cholangiocarcinoma with FGFR2 and/or FGFR3 mutation. In another preferred embodiment, the cholangiocarcinoma refers to cholangiocarcinoma with any one of FGFR2 N549H, FGFR2 V564F and FGFR3 K650E or any combination thereof.

In another further embodiment, the cholangiocarcinoma refers to drug-resistant cholangiocarcinoma that is positive for FGFR aberration but not responsive to an FGFR inhibitor, or drug-resistant cholangiocarcinoma after administration of an FGFR inhibitor. In a preferred embodiment, the cholangiocarcinoma refers to drug-resistant cholangiocarcinoma with FGFR2 and/or FGFR3 aberration.

In another further embodiment, the cholangiocarcinoma refers to any one of intrahepatic cholangiocarcinoma, perihilar cholangiocarcinoma and distal cholangiocarcinoma or any combination thereof. In a preferred embodiment, the cholangiocarcinoma refers to perihilar cholangiocarcinoma. In a preferred embodiment, the cholangiocarcinoma refers to distal cholangiocarcinoma. In a preferred embodiment, the cholangiocarcinoma refers to intrahepatic cholangiocarcinoma. In another preferred embodiment, the intrahepatic cholangiocarcinoma refers to intrahepatic cholangiocarcinoma with FGFR2 aberration. In another preferred embodiment, the intrahepatic cholangiocarcinoma refers to intrahepatic cholangiocarcinoma with FGFR2 fusion. In another preferred embodiment, the intrahepatic cholangiocarcinoma refers to intrahepatic cholangiocarcinoma with non-FGFR aberration.

In one embodiment, the cholangiocarcinoma further comprises cholangiocarcinoma mediated by other mechanisms, including Aurora-kinase-mediated cholangiocarcinoma and cholangiocarcinoma caused by abnormal IL-6-mediated JAK-STAT signaling pathway.

In one embodiment, the compound of general formula (I) or the pharmaceutically acceptable salt, the stereoisomer and the crystal form thereof is administered in a therapeutically effective amount to a patient or subject in need thereof.

In one embodiment, a therapeutically effective amount of the compound of general formula (I) or the pharmaceutically acceptable salt, the stereoisomer and the crystal form thereof may be further prepared with one or more pharmaceutically acceptable carriers into any pharmaceutically acceptable pharmaceutical formulation.

In one embodiment, the pharmaceutical formulation may comprise one or more pharmaceutically acceptable carriers, and may be administered to a patient or subject in need of such treatment by oral, parenteral, rectal, or transpulmonary administration, and the like. For oral administration, the pharmaceutical composition can be prepared into a conventional solid formulation, such as tablets, capsules, pills and granules; or can be prepared into an oral liquid formulation, such as oral solutions, oral suspensions and syrups. In the preparation of an oral formulation, an appropriate filler, binder, disintegrant, lubricant and the like may be added. For parenteral administration, the pharmaceutical composition can be prepared into an injection, including a solution injection, a sterile powder for injection and a concentrated solution for injection. The injection can be produced by a conventional method existing in the pharmaceutical field, and during the preparation process, no additive may be added, or an appropriate additive may be added according to the property of the medicament. For rectal administration, the pharmaceutical composition can be prepared into a suppository and the like. For transpulmonary administration, the pharmaceutical composition can be prepared into an inhalant, a spray or the like.

In one embodiment, a therapeutically effective amount of a compound of general formula (I) or a pharmaceutically acceptable salt, a stereoisomer and a crystal form thereof can further be administered in combination with one or more second therapeutically active agents to a patient or subject in need thereof.

In a further embodiment, the second therapeutically active agent is an antimetabolite, a growth factor inhibitor, a mitotic inhibitor, an anti-tumor hormone, an alkylating agent, metallic platinum, a topoisomerase inhibitor, a hormonal drug, an immunomodulator, a tumor suppressor gene, a cancer vaccine, or an immune checkpoint inhibitor.

In one embodiment, the compound of general formula (I) or the pharmaceutically acceptable salt, the stereoisomer and the crystal form thereof and the second therapeutically active agent are administered to a patient or subject in need of treatment in combination.

In one embodiment, the compound of general formula (I) or the pharmaceutically acceptable salt, the stereoisomer and the crystal form thereof and the second therapeutically active agent are administered to a patient or subject in need of treatment sequentially, simultaneously or in a combined formulation.

In a further embodiment, the patient or subject is a mammal. In a preferred embodiment, the patient or subject is a human.

In a fourth aspect of the present invention, provided is a method for treating biliary tract cancer, comprising administering to a patient in need thereof a therapeutically effective amount of a compound of formula (I) or a pharmaceutically acceptable salt, a stereoisomer and a crystal form thereof,

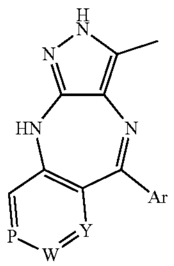

(I)

wherein the variables in the above general formula (I) are as defined above.

In one embodiment, Ar is phenyl optionally substituted with 1-3 $R_6$, and each $R_6$ is independently selected from hydrogen and halogen;

Y is $CR_3$;

P is $CR_4$;

W is N;

$R_3$ is hydrogen;

$R_4$ is selected from $-(CH_2)_n$-(5-6) membered monocyclic heterocyclyl and $-(CH_2)_n$-(7-11) membered fused heterocyclyl, wherein n=0-6, a ring-forming S atom in the heterocyclyl is optionally oxidized to S(O) or $S(O)_2$, a ring-forming C atom is optionally oxidized to C(O), and the heterocyclyl is optionally substituted with one to more substituents independently selected from $C_{1-3}$ alkyl and $C_{3-6}$ cycloalkyl.

In a further embodiment, the (5-6) membered monocyclic heterocyclyl is (5-6) membered saturated monocyclic heterocyclyl, and the (7-11) membered fused heterocyclyl is (7-11) membered saturated fused heterocyclyl. In a preferred embodiment, the (7-11) membered fused heterocyclyl is (7-11) membered saturated ortho-fused heterocyclyl, (7-11) membered saturated spiro-heterocyclyl or (7-11) membered saturated bridged heterocyclyl.

In one embodiment, the (5-11) membered heterocyclyl is

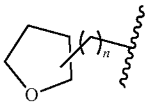
,
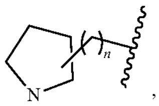
,
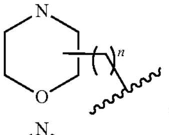
,
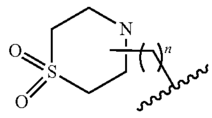
,
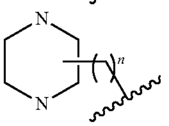
,
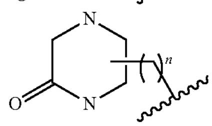
, -continued

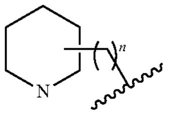, 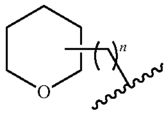,

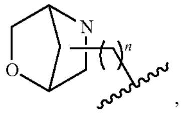, 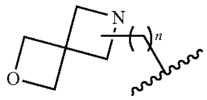 or

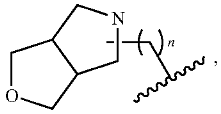, and n=0-3, wherein the heterocyclyl is optionally substituted with one to more substituents independently selected from $C_{1-3}$ alkyl and $C_{3-6}$ cycloalkyl. In a preferred embodiment, the (5-11) membered heterocyclyl is

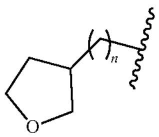, 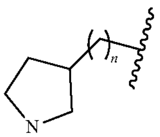, 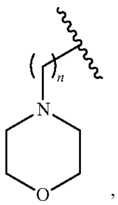,

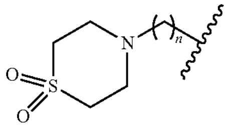, 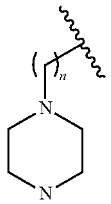,

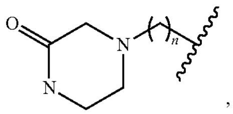, 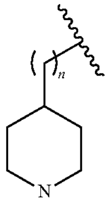,

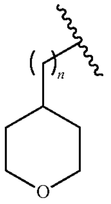, 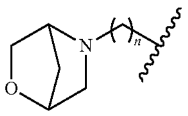,

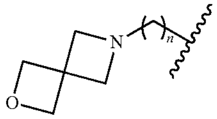 or

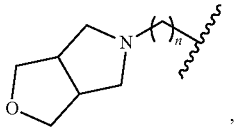, and n=0-3, wherein the heterocyclyl is optionally substituted with one to more substituents independently selected from $C_{1-3}$ alkyl and $C_{3-6}$ cycloalkyl.

In one embodiment, the compound of general formula (I) is a compound shown in Table 1 or a pharmaceutically acceptable salt, a stereoisomer and a crystal form thereof.

In a preferred embodiment, the compound of general formula (I) is

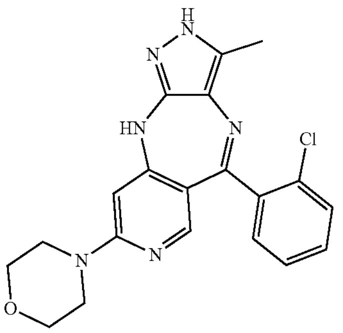

or a pharmaceutically acceptable salt, a stereoisomer and a crystal form thereof.

In one embodiment, the biliary tract cancer refers to cholangiocarcinoma.

In a further embodiment, the cholangiocarcinoma refers to an FGFR-mediated cholangiocarcinoma. In a preferred embodiment, the FGFR-mediated cholangiocarcinoma refers to cholangiocarcinoma mediated by any one of FGFR1, FGFR2 and FGFR3 or any combination thereof.

In another further embodiment, the cholangiocarcinoma refers to a cholangiocarcinoma with non-FGFR aberration. In a preferred embodiment, the cholangiocarcinoma with non-FGFR aberration refers to cholangiocarcinoma with non-FGFR2 aberration.

In another further embodiment, the cholangiocarcinoma refers to a cholangiocarcinoma with FGFR aberration. In a preferred embodiment, the cholangiocarcinoma with FGFR aberration refers to a cholangiocarcinoma with FGFR2 and/or FGFR3 aberration.

In still further embodiments, the cholangiocarcinoma refers to cholangiocarcinoma with any one of FGFR fusion, FGFR mutation and FGFR overexpression or any combination thereof. Wherein the FGFR mutation comprises an FGFR point mutation and an FGFR insertion/deletion mutation.

In a preferred embodiment, the cholangiocarcinoma refers to cholangiocarcinoma with any one of FGFR2 fusion, FGFR2 and/or FGFR3 mutation and FGFR overexpression or any combination thereof. In another preferred embodiment, the cholangiocarcinoma refers to cholangiocarcinoma with FGFR2 fusion. In another preferred embodiment, the cholangiocarcinoma refers to cholangiocarcinoma with FGFR2 and/or FGFR3 mutation. In another preferred embodiment, the cholangiocarcinoma refers to cholangiocarcinoma with any one of FGFR2 N549H, FGFR2 V564F and FGFR3 K650E or any combination thereof.

In another further embodiment, the cholangiocarcinoma refers to drug-resistant cholangiocarcinoma that is positive for FGFR aberration but not responsive to an FGFR inhibitor, or drug-resistant cholangiocarcinoma after administration of an FGFR inhibitor. In a preferred embodiment, the cholangiocarcinoma refers to drug-resistant cholangiocarcinoma with FGFR2 and/or FGFR3 aberration.

In another further embodiment, the cholangiocarcinoma refers to any one of intrahepatic cholangiocarcinoma, perihilar cholangiocarcinoma and distal cholangiocarcinoma or any combination thereof. In a preferred embodiment, the cholangiocarcinoma refers to perihilar cholangiocarcinoma. In a preferred embodiment, the cholangiocarcinoma refers to distal cholangiocarcinoma. In a preferred embodiment, the cholangiocarcinoma refers to intrahepatic cholangiocarcinoma. In another preferred embodiment, the intrahepatic cholangiocarcinoma refers to intrahepatic cholangiocarcinoma with FGFR2 aberration. In another preferred embodiment, the intrahepatic cholangiocarcinoma refers to intrahepatic cholangiocarcinoma with FGFR2 fusion. In another preferred embodiment, the intrahepatic cholangiocarcinoma refers to intrahepatic cholangiocarcinoma with non-FGFR aberration.

In one embodiment, the cholangiocarcinoma further comprises cholangiocarcinoma mediated by other mechanisms, including Aurora-kinase-mediated cholangiocarcinoma and cholangiocarcinoma caused by abnormal IL-6-mediated JAK-STAT signaling pathway.

In one embodiment, the therapeutically effective amount of the compound of general formula (I) or a pharmaceutically acceptable salt, a stereoisomer and a crystal form thereof may be further prepared with one or more pharmaceutically acceptable carriers into any pharmaceutically acceptable pharmaceutical formulation.

In one embodiment, the pharmaceutical formulation may comprise one or more pharmaceutically acceptable carriers, and may be administered to a patient or subject in need of such treatment by oral, parenteral, rectal, or transpulmonary administration, and the like. For oral administration, the pharmaceutical composition can be prepared into a conventional solid formulation, such as tablets, capsules, pills and granules; or can be prepared into an oral liquid formulation, such as oral solutions, oral suspensions and syrups. In the preparation of an oral formulation, an appropriate filler, binder, disintegrant, lubricant and the like may be added. For parenteral administration, the pharmaceutical composition can be prepared into an injection, including a solution injection, a sterile powder for injection and a concentrated solution for injection. The injection can be produced by a conventional method existing in the pharmaceutical field, and during the preparation process, no additive may be added, or an appropriate additive may be added according to the property of the medicament. For rectal administration, the pharmaceutical composition can be prepared into a suppository and the like. For transpulmonary administration, the pharmaceutical composition can be prepared into an inhalant, a spray or the like.

In one embodiment, the method further comprises administering to a patient or subject in need thereof a therapeutically effective amount of a compound of general formula (I) or a pharmaceutically acceptable salt, a stereoisomer and a crystal form thereof and one or more second therapeutically active agents.

In a further embodiment, the second therapeutically active agent is an antimetabolite, a growth factor inhibitor, a mitotic inhibitor, an anti-tumor hormone, an alkylating agent, metallic platinum, a topoisomerase inhibitor, a hormonal drug, an immunomodulator, a tumor suppressor gene, a cancer vaccine, or an immune checkpoint inhibitor.

In one embodiment, the compound of general formula (I) or the pharmaceutically acceptable salt, the stereoisomer and the crystal form thereof and the second therapeutically active agent are administered to a patient or subject in need of treatment in combination.

In one embodiment, the compound of general formula (I) or the pharmaceutically acceptable salt, the stereoisomer and the crystal form thereof and the second therapeutically active agent are administered to a patient or subject in need of treatment sequentially, simultaneously or in a combined formulation.

In a further embodiment, the patient or subject is a mammal. In a preferred embodiment, the patient or subject is a human.

In a fifth aspect of the present invention, provided is a pharmaceutical composition for use in the treatment of biliary tract cancer, comprising a therapeutically effective amount of a compound of formula (I) or a pharmaceutically acceptable salt, a stereoisomer and a crystal form thereof, and optionally comprising a pharmaceutically acceptable carrier:

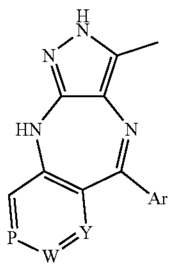

(I)

wherein the variables in the above general formula (I) are as defined above.

In one embodiment, Ar is phenyl optionally substituted with 1-3 $R_6$, and each $R_6$ is independently selected from hydrogen and halogen;

Y is $CR_3$;

P is $CR_4$;

W is N;

$R_3$ is hydrogen;

$R_4$ is selected from $-(CH_2)_n$-(5-6) membered monocyclic heterocyclyl and $-(CH_2)_n$-(7-11) membered fused heterocyclyl, wherein n=0-6, a ring-forming S atom in the heterocyclyl is optionally oxidized to S(O) or $S(O)_2$, a ring-forming C atom is optionally oxidized to C(O), and the heterocyclyl is optionally substituted with one to more substituents independently selected from $C_{1-3}$ alkyl and $C_{3-6}$ cycloalkyl.

In a further embodiment, the (5-6) membered monocyclic heterocyclyl is (5-6) membered saturated monocyclic heterocyclyl, and the (7-11) membered fused heterocyclyl is (7-11) membered saturated fused heterocyclyl. In a preferred embodiment, the (7-11) membered fused heterocyclyl is (7-11) membered saturated ortho-fused heterocyclyl, (7-11) membered saturated spiro-heterocyclyl or (7-11) membered saturated bridged heterocyclyl.

In one embodiment, the (5-11) membered heterocyclyl is

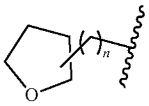,
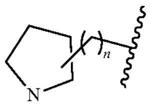,
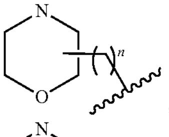,
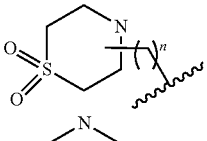,
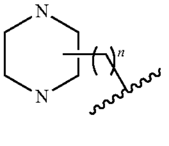,
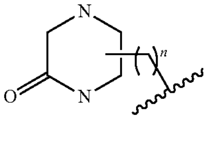,

-continued

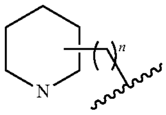, 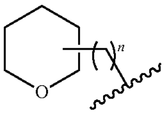,

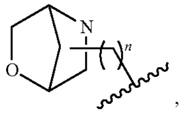, 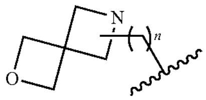 or

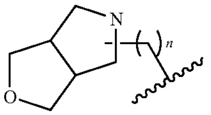, and n=0-3, wherein the heterocyclyl is optionally substituted with one to more substituents independently selected from $C_{1-3}$ alkyl and $C_{3-6}$ cycloalkyl. In a preferred embodiment, the (5-11) membered heterocyclyl is

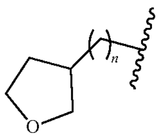, 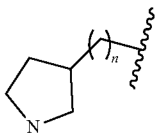, 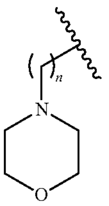,

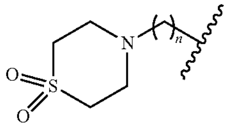, 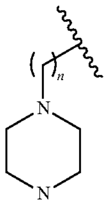,

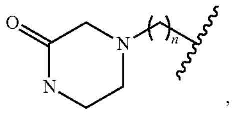, 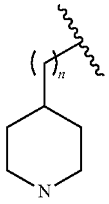,

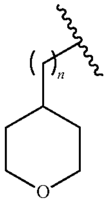, 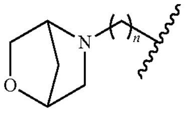,

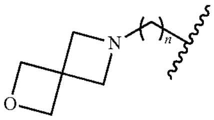 or

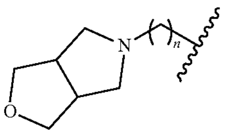, and n=0-3, wherein the heterocyclyl is optionally substituted with one to more substituents independently selected from $C_{1-3}$ alkyl and $C_{3-6}$ cycloalkyl.

In one embodiment, the compound of general formula (I) is a compound shown in Table 1 or a pharmaceutically acceptable salt, a stereoisomer and a crystal form thereof.

In a preferred embodiment, the compound of general formula (I) is

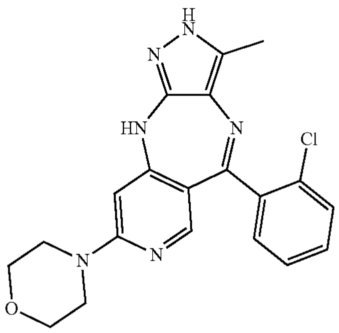

or a pharmaceutically acceptable salt, a stereoisomer and a crystal form thereof.

In one embodiment, the biliary tract cancer refers to cholangiocarcinoma.

In a further embodiment, the cholangiocarcinoma refers to an FGFR-mediated cholangiocarcinoma. In a preferred embodiment, the FGFR-mediated cholangiocarcinoma refers to cholangiocarcinoma mediated by any one of FGFR1, FGFR2 and FGFR3 or any combination thereof.

In another further embodiment, the cholangiocarcinoma refers to a cholangiocarcinoma with non-FGFR aberration. In a preferred embodiment, the cholangiocarcinoma with non-FGFR aberration refers to cholangiocarcinoma with non-FGFR2 aberration.

In another further embodiment, the cholangiocarcinoma refers to a cholangiocarcinoma with FGFR aberration. In a preferred embodiment, the cholangiocarcinoma with FGFR aberration refers to a cholangiocarcinoma with FGFR2 and/or FGFR3 aberration.

In still further embodiments, the cholangiocarcinoma refers to cholangiocarcinoma with any one of FGFR fusion, FGFR mutation and FGFR overexpression or any combination thereof. Wherein the FGFR mutation comprises an FGFR point mutation and an FGFR insertion/deletion mutation.

In a preferred embodiment, the cholangiocarcinoma refers to cholangiocarcinoma with any one of FGFR2 fusion, FGFR2 and/or FGFR3 mutation and FGFR overexpression or any combination thereof. In another preferred embodiment, the cholangiocarcinoma refers to cholangiocarcinoma with FGFR2 fusion. In another preferred embodiment, the cholangiocarcinoma refers to cholangiocarcinoma with FGFR2 and/or FGFR3 mutation. In another preferred embodiment, the cholangiocarcinoma refers to cholangiocarcinoma with any one of FGFR2 N549H, FGFR2 V564F and FGFR3 K650E or any combination thereof.

In another further embodiment, the cholangiocarcinoma refers to drug-resistant cholangiocarcinoma that is positive for FGFR aberration but not responsive to an FGFR inhibitor, or drug-resistant cholangiocarcinoma after administration of an FGFR inhibitor. In a preferred embodiment, the cholangiocarcinoma refers to drug-resistant cholangiocarcinoma with FGFR2 and/or FGFR3 aberration.

In another further embodiment, the cholangiocarcinoma refers to any one of intrahepatic cholangiocarcinoma, perihilar cholangiocarcinoma and distal cholangiocarcinoma or any combination thereof. In a preferred embodiment, the cholangiocarcinoma refers to perihilar cholangiocarcinoma. In a preferred embodiment, the cholangiocarcinoma refers to distal cholangiocarcinoma. In a preferred embodiment, the cholangiocarcinoma refers to intrahepatic cholangiocarcinoma. In another preferred embodiment, the intrahepatic cholangiocarcinoma refers to intrahepatic cholangiocarcinoma with FGFR2 aberration. In another preferred embodiment, the intrahepatic cholangiocarcinoma refers to intrahepatic cholangiocarcinoma with FGFR2 fusion. In another preferred embodiment, the intrahepatic cholangiocarcinoma refers to intrahepatic cholangiocarcinoma with non-FGFR aberration.

In one embodiment, the cholangiocarcinoma further comprises cholangiocarcinoma mediated by other mechanisms, including Aurora-kinase-mediated cholangiocarcinoma and cholangiocarcinoma caused by abnormal IL-6-mediated JAK-STAT signaling pathway.

In one embodiment, the compound of general formula (I) or a pharmaceutically acceptable salt, a stereoisomer and a crystal form thereof can be further prepared with one or more pharmaceutically acceptable carriers into any pharmaceutically acceptable pharmaceutical formulation.

In one embodiment, the pharmaceutical formulation may comprise one or more pharmaceutically acceptable carriers, and may be administered to a patient or subject in need of such treatment by oral, parenteral, rectal, or transpulmonary administration, and the like. For oral administration, the pharmaceutical composition can be prepared into a conventional solid formulation, such as tablets, capsules, pills and granules; or can be prepared into an oral liquid formulation, such as oral solutions, oral suspensions and syrups. In the preparation of an oral formulation, an appropriate filler, binder, disintegrant, lubricant and the like may be added. For parenteral administration, the pharmaceutical composition can be prepared into an injection, including a solution injection, a sterile powder for injection and a concentrated solution for injection. The injection can be produced by a conventional method existing in the pharmaceutical field, and during the preparation process, no additive may be added, or an appropriate additive may be added according to the property of the medicament. For rectal administration, the pharmaceutical composition can be prepared into a suppository and the like. For transpulmonary administration, the pharmaceutical composition can be prepared into an inhalant, spray or the like.

In one embodiment, the pharmaceutical composition further comprises one or more second therapeutically active agents.

In a further embodiment, the second therapeutically active agent is an antimetabolite, a growth factor inhibitor, a mitotic inhibitor, an anti-tumor hormone, an alkylating agent, metallic platinum, a topoisomerase inhibitor, a hormonal drug, an immunomodulator, a tumor suppressor gene, a cancer vaccine, or an immune checkpoint inhibitor.

In one embodiment, the compound of general formula (I) or the pharmaceutically acceptable salt, the stereoisomer and the crystal form thereof and the second therapeutically active agent are administered to a patient or subject in need of treatment in combination.

In one embodiment, the compound of general formula (I) or the pharmaceutically acceptable salt, the stereoisomer and the crystal form thereof and the second therapeutically active agent are administered to a patient or subject in need of treatment sequentially, simultaneously or in a combined formulation.

In a further embodiment, the patient or subject is a mammal. In a preferred embodiment, the patient or subject is a human.

3. Definition

The "halogen" described herein refers to fluorine, chlorine, bromine, iodine and the like, and preferably fluorine and chlorine.

The "halogenated" described herein means that any hydrogen atom in a substituent can be substituted with one or more identical or different halogen. "Halogen" is defined as above.

The "cyano" described herein referred to the —CN group.

The "amino" described herein refers to the $—NH_2$ group.

As described herein, "$C_{1-4}$ alkyl" refers to a linear or branched alkyl derived from a hydrocarbon moiety having 1 to 4 carbon atoms by removing one hydrogen atom, such as methyl, ethyl, n-propyl, isopropyl, n-butyl, isobutyl, sec-butyl, or tert-butyl. The "$C_{1-3}$ alkyl" refers to the above alkyl having 1 to 3 carbon atoms.

The "$C_{3-6}$ cycloalkyl" described herein refers to a monocyclic cycloalkyl or bicyclic cycloalkyl system or a polycyclic cycloalkyl system having 3 to 6 carbon atoms. These groups are saturated but not aromatic, including monocyclic and fused ring structures which can be formed, unless otherwise specified. Examples thereof include, but are not limited to: cyclopropyl, cyclobutyl, cyclopentyl, cyclohexyl, bicyclo[2.2.2]hexane, and bicyclo[3.2.1]hexane.

The "5-11 membered heterocyclyl" described herein refers to a non-aromatic cyclic group having 5 to 11 ring carbon atoms, wherein at least one ring carbon atom is substituted with one or more heteroatoms selected from O, S and N, and preferably 1 to 3 heteroatoms, and ring-forming atoms including carbon atoms, nitrogen atoms and sulfur atoms may be oxidized.

The "heterocyclyl" refers to a monocyclic heterocyclyl or bicyclic heterocyclyl system or a polycyclic heterocyclyl system, including saturated and partially saturated heterocyclyl, but not including aromatic rings. Unless otherwise specified, the "5-11 membered heterocyclyl" described herein includes monocyclic and fused ring structures which can be formed.

The monocyclic heterocyclyl may be 5-7 membered heterocyclyl, 5-6 membered heterocyclyl, 5-6 membered oxygen-containing heterocyclyl, 5-6 membered nitrogen-containing heterocyclyl, 5-6 membered saturated heterocyclyl and the like. Examples of 5-6 membered monocyclic heterocyclyl described herein include, but are not limited to, tetrahydrofuranyl, tetrahydropyrrolyl, tetrahydrothienyl, imidazolidinyl, pyrazolidinyl, 1,2-oxazolidinyl, 1,3-oxazolidinyl, 1,2-thiazolidinyl, 1,3-thiazolidinyl, tetrahydro-2H-pyranyl, tetrahydro-2H-thiopyranyl, piperidinyl, piperazinyl, morpholinyl, 1,4-dioxanyl, 1,4-oxathianyl, 4,5-dihydroisoxazolyl, 4,5-dihydrooxazolyl, 2,5-dihydrooxazolyl, 2,3-dihydrooxazolyl, 3,4-dihydro-2H-pyrrolyl, 2,3-dihydro-1H-pyrrolyl, 2,5-dihydro-1H-imidazolyl, 4,5-dihydro-1H-imidazolyl, 4,5-dihydro-1H-pyrazolyl, 4,5-dihydro-3H-pyrazolyl, 4,5-dihydrothiazolyl, 2,5-dihydrothiazolyl, 2H-pyranyl, 4H-pyranyl, 2H-thiopyranyl, 4H-thiopyranyl, 2,3,4,5-tetrahydropyridyl, 1,2-isoxazolyl, 1,4-isoxazolyl, 6H-1,3-oxazinyl, or the like.

The fused heterocyclyl includes ortho-fused heterocyclyl, spiro-heterocyclyl and bridged heterocyclyl, which may be saturated, partially saturated or unsaturated, but non-aromatic. Unless otherwise specified, the 7-11 membered fused heterocyclyl described herein includes ortho-fused, spiro and bridged structures which can be formed.

The ortho-fused heterocyclyl may be 7-11 membered ortho-fused cyclyl, and preferably 7-11 membered saturated ortho-fused cyclyl; examples of which include, but are not limited to: 3,6-diazabicyclo[3.2.0]heptyl, 3,8-diazabicyclo [4.2.0]octyl, 3,7-diazabicyclo[4.2.0]octyl, octahydropyrrolo [3,4-c]pyrroly, octahydropyrrolo[3,4-b]pyrroly, octahydropyrrolo[3,4-b][1,4]oxazinyl, octahydro-1H-pyrrolo[3,4-c] pyridinyl, 2,3-dihydrobenzofuran-2-yl, 2,3-dihydrobenzofuran-3-yl, indolin-1-yl, indolin-2-yl, indolin 3-yl, 2,3-dihydrobenzothien-2-yl, octahydro-1H-indolyl, and octahydrobenzofuranyl.

The spiro-heterocyclyl may be 7-11 membered spiro-heterocyclyl, and preferably 7-11 membered saturated spiro-heterocyclyl; examples of which include, but are not limited to:

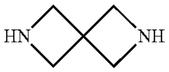,
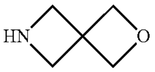,
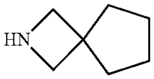,
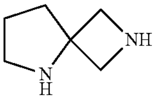,
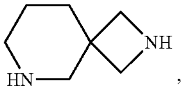,
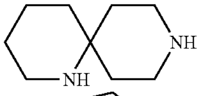,
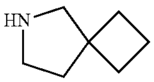,
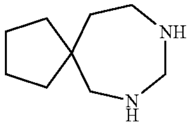,
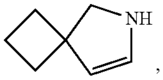,
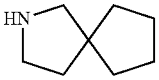, and
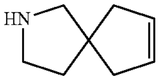, The bridged heterocyclyl may be 7-11 membered bridged heterocyclyl, and preferably 7-11 membered saturated bridged heterocyclyl; examples of which include, but are not limited to:

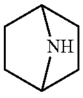,
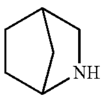,
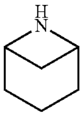,
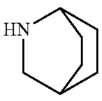,
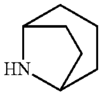,
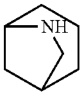,
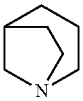,
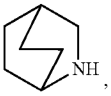,
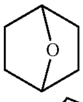,
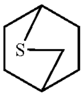,
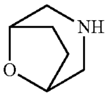, and
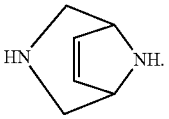.

The "pharmaceutically acceptable salt" described herein refers to both pharmaceutically acceptable acid and base addition salts and solvates. Such pharmaceutically acceptable salts include salts of the following acids: hydrochloric acid, phosphoric acid, hydrobromic acid, sulfuric acid, sulfurous acid, formic acid, toluenesulfonic acid, methanesulfonic acid, nitric acid, benzoic acid, citric acid, tartaric acid, maleic acid, hydroiodic acid, alkanoic acid (such as acetic acid, HOOC—$(CH_2)$n—COOH (wherein n is 0-4)), and the like. Such pharmaceutically acceptable salts further include salts of the following bases: sodium, potassium, calcium, ammonium, and the like. Those skilled in the art know a variety of pharmaceutically acceptable non-toxic addition salts.

All numerical ranges described herein include both endpoints of the ranges, all integers within the range and subranges formed by these integers. For example, "5-11 membered" includes 5, 6, 7, 8, 9, 10 or 11 membered, "5-6 membered" includes 5 or 6 membered, and "7-11 membered" includes 7, 8, 9, 10 or 11 membered and so on.

The "one to more" as described herein with respect to a substituent refers to the number of substituents with which all positions can be chemically substituted in the substituted group, preferably 1 to 6, more preferably 1 to 5, more preferably 1 to 3, and more preferably 1 to 2.

The "crystal form" described herein may be prepared from the compound of general formula (I) by conventional methods for preparing crystal forms used in the art.

The "stereoisomer" of the compound of general formula (I) described herein means that an enantiomer can be formed when asymmetric carbon atoms are present in the compound of general formula (I); a cis-trans isomer can be formed when a carbon-carbon double bond or a ring structure is present in the compound; a tautomer can be formed when a ketone or oxime is present in the compound. All enantiomers, diastereomers, racemates, cis-trans isomers, tautomers, geometric isomers and epimers of the compound of general formula (I) as well as mixtures thereof are included in the scope of the present invention.

The preparation of the compound of general formula (I) described herein can be found in the detailed description of WO2018108079A1.

The "therapeutically effective amount" described herein refers to an amount of the aforementioned compound or the pharmaceutically acceptable salt, the stereoisomer and the crystal form thereof and/or the pharmaceutical formulation that, when administered to a patient, is at least capable of alleviating symptoms of the patient's condition. An actual amount comprising the "therapeutically effective amount" will vary depending on a variety of circumstances, including, but not limited to, the particular condition being treated, the severity of the condition, the physique and health of the patient, and the route of administration. The appropriate amount can be readily determined by skilled medical practitioners using methods known in the medical field.

The "mammal" described herein refers to a group of animals of the class mammalia of the subphylum vertebrates, which are lactated by the mammary glands to suckle young children. It can be divided into human mammals and non-human mammals. Examples of non-human mammals include, but are not limited to, tigers, leopards, wolves, deer, giraffes, minks, monkeys, orangutans, tapirs, foxes, sloths, bears, koala bears, polar bears, elephants, musk-oxen, rhinoceros, sea cattle, lions, red pandas, pandas, warthogs, antelopes, koalas, lynxes, pangolins, anteaters, otters, dolphins, walruses, seals, whales, platypuses, hedgehogs, kangaroos, hippopotamus, weasels, badgers, leopard cats, horses, cattle, sheep, mules, donkeys, dogs, mice, cats, and rabbits.

The "pharmaceutically acceptable carrier" described herein includes, but is not limited to, solid carriers and liquid carriers. Suitable solid carriers include, but are not limited to, cellulose, glucose, lactose, mannitol, magnesium stearate, magnesium carbonate, sodium carbonate, sodium saccharin, sucrose, dextrin, talc, starch, pectin, gelatin, tragacanth, arabic gum, sodium alginate, p-hydroxylbenzoate, methylcellulose, sodium carboxymethyl cellulose, low-melting wax, cocoa butter, and the like. Suitable liquid carriers include, but are not limited to, water, ethanol, polyol (such as glycerin, propylene glycol and liquid polyethylene glycol), vegetable oil, glyceride and mixtures thereof.

The "FGFR inhibitor" described herein is a small-molecule inhibitor drug which is available on the market or is in clinical research or preclinical research and is proved to be capable of targeting FGFR kinase to play a role in treating cancer, and in particular to a drug for treating cholangiocarcinoma, such as: Erdafitinib, BGJ-398, TAS-120 and INCB-054828.

Beneficial Effects of Present Invention

The compound of general formula (I) or a pharmaceutically acceptable salt, a stereoisomer and a crystal form thereof can effectively treat biliary tract cancer, and particularly has a remarkable treatment effect on cholangiocarcinoma. Researches show that the compound has a good treatment effect on cholangiocarcinoma with non-FGFR aberration, cholangiocarcinoma with FGFR aberration, various FGFR drug-resistant cholangiocarcinomas and cholangiocarcinoma of various anatomical sites.

DETAILED DESCRIPTION

In order to make the objective, technical solutions and advantages of the present invention more apparent, the present invention is further described in detail below. It should be apparent that the examples described herein are only some examples of the present invention, but not all examples. Based on the examples of the present invention, all other examples obtained by those of ordinary skill in the art without creative work shall fall within the protection scope of the present invention.

The abbreviations and English expressions used in the present invention have the following meanings:

TABLE 2

Abbreviations and English expressions

| Abbreviation/English | Meaning |
|---|---|
| DMSO | Dimethyl sulfoxide |
| MOPS | 3-morpholinopropanesulfonic acid |
| EDTA | Ethylenediaminetetraacetic acid |
| $MnCl_2$ | Manganese chloride |
| MC | Methylcellulose |
| ATP | Adenosine triphosphate |
| Glu | Glutamic acid |
| Tyr | Tyrosine |
| PEG | Polyethylene glycol |
| Qd | Administration once daily |
| Qw | Administration once a week |
| BiW | Administration twice a week |

Experimental Example 1: Assay on Inhibitory Activity of Compounds of the Present Invention Against FGFR Wild-Type Enzyme Test samples: the compounds of the present invention, which have structures shown in Table 1 and are prepared as described in the embodiments of WO2018108079A1.

Experiment Method (1) Preparation of the Compound Plate

The compounds were each dissolved in DMSO to prepare stock solutions with a maximum concentration of 500 μM. The compound stock solutions were diluted with DMSO to final concentrations of 500, 150, 50, 15, 5, 1.5, 0.5, 0.15, 0.05 μM to obtain compound working solutions (50×).

(2) Experimental Procedures a) Preparation of Different Reaction Systems

FGFR1(h) was dissolved in 8 mM MOPS (pH 7.0), 0.2 mM EDTA and 250 μM KKKSPGEYVNIEFG;

FGFR2(h) was dissolved in 8 mM MOPS (pH 7.0), 0.2 mM EDTA, 2.5 mM $MnCl_2$ and 0.1 mg/mL poly (Glu, Tyr) (4:1);

FGFR3(h) was dissolved in 8 mM MOPS (pH 7.0), 0.2 mM EDTA, 10 mM $MnCl_2$ and 0.1 mg/mL poly (Glu, Tyr) (4:1);

b) Enzymatic Reaction

The reaction was initiated by the addition of 10 mM magnesium acetate and 10 μM [$\gamma$-$^{33}$P]-ATP. After incubation at room temperature for 40 min, the reaction was stopped by using a 3% (v/v) phosphoric acid solution. 10 μL of the reaction solution was pipetted onto P30 filter paper, washed 3 times with 75 mM phosphoric acid solution for 5 min each time, dried and counted by scintillation. 2% (v/v) DMSO was taken as a positive control (Max) instead of the compound solutions; high concentration positive control inhibitor (10 μM Staurosporine) was taken as a negative control (Min) instead of the compound solutions.

Test Results:

TABLE 3

Inhibitory activity of compounds of the present invention against wild-type FGFRs ($IC_{50}$)

| Test samples | FGFR1 (nM) | FGFR2 (nM) | FGFR3 (nM) |
|---|---|---|---|
| Compound 29 | 2 | 3 | 5 |

It can be seen from the experimental results in Table 3 that the compounds of the present invention can target FGFR1-3, have a good inhibitory activity against FGFR1-3, and have good clinical application potential in the aspect of treating diseases mediated by FGFR1-3.

Experimental Example 2: Assay on Inhibitory Activity of Compounds of the Present Invention Against Wild-Type and Mutant FGFR Test samples: the compounds of the present invention, which have structures shown in Table 1 and are prepared as described in the embodiments of WO2018108079A1.

TABLE 4

| Names and sources of enzymes/reagents | | |
|---|---|---|
| Abbreviations | Name | Source |
| FGFR2 WT | Wild-type FGFR2 enzyme | Invitrogen |
| FGFR2 N549H | N549H gene mutant FGFR2 enzyme | Signalchem |
| FGFR2 V564F | V564F gene mutant FGFR2 enzyme | Signalchem |
| FGFR3 WT | Wild-type FGFR3 enzyme | Invitrogen |
| FGFR3 K650E | K650E gene mutant FGFR3 enzyme | Signalchem |
| HTRF KinEASE-TK kit | Homogeneous time-resolved fluorescence method kit | Cisbio |
| BIBF 1120 | Nintedanib | ChemExpress |

Experiment Method (1) Preparation of the Compound Plate

The compounds were dissolved in DMSO and 3-fold diluted with DMSO to obtain 10 serially diluted stock solutions. The stock solutions were added into a 384-well plate to obtain a 3-fold diluted series of 10 concentrations of the compound starting from 10 μm.

(2) Experimental Procedures

Different enzyme solutions (2×) were prepared, transferred into the 384-well plate, incubated with the compound solutions with different concentrations for 10 min at room temperature, and a mixed solution (2×) of biotinylated tyrosine kinase substrate/ATP was added to activate the reaction. After incubation for 50 min at room temperature, an HTRF detection reagent and a corresponding kinase antibody cryptate were added, and after incubation for 1 h at room temperature, fluorescence readings at 615 nm (cryptate) and 665 nm (HTRF detection reagent) were detected by using an Envision 2104 multifunctional microplate reader. 10 μM BIBF-1120 was taken as a compound positive control (PC) instead of the compound solutions, and 0.1% (v/v) DMSO was taken as a solvent negative control (VC) instead of the compound solutions.

(3) Data Processing

The fluorescence ratio of 665/615 nm was calculated, and the enzyme activity inhibition rate (%) was calculated according to the following formula:

$$\text{Inhibition rate } \% = 100 - \frac{\text{Fluorescence ratio of compounds} - \text{Mean fluorescence ratio of } PC}{\text{Mean fluorescence ratio of } VC - \text{Mean fluorescence ratio of } PC} \times 100$$

$IC_{50}$ values were fitted using GraphPad 6.0 based on inhibition rates of compounds with different concentrations.

Test Results:

TABLE 5

| Inhibitory Activity of Compounds of the Present Invention Against FGFR enzyme ($IC_{50}$) | | |
|---|---|---|
| Test samples | Enzymes | $IC_{50}$ (nM) |
| Compound 29 | FGFR2 WT | 0.5 |
| | FGFR2 N549H | 1.9 |
| | FGFR2 V564F | 0.7 |
| Compound 29 | FGFR3 WT | 1.0 |
| | FGFR3 K650E | 1.7 |

It can be seen from the experimental results in Table 5 that the compounds of the present invention have an obvious inhibitory effect on both wild-type and mutant FGFR2 and FGFR3, which indicates that the compounds of the present invention have better clinical application potential in treating diseases mediated by wild-type and/or mutant FGFR, such as cholangiocarcinoma.

Experimental Example 3: Cholangiocarcinoma Organoid Experiment of Compounds of the Present Invention Test samples: the compounds of the present invention, which have structures shown in Table 1 and are prepared as described in the embodiments of WO2018108079A1.

Organoid information: Human distal cholangiocarcinoma (dCC) from K2 Oncology Co. Ltd., Beijing, code KOBD-002

TABLE 6

| Names and sources of reagents and instruments | |
|---|---|
| Name | Source/model No. |
| 96-channel high-throughput full-automatic liquid workstation | NAYO N96 |
| Microplate reader | BMG FLUOstar |
| Fetal bovine serum | Gibco |
| Penicillin/streptomycin double-antibody | Gibco 15140122 |
| Pancreatin | Gibco 12604013 |
| Cell Viability fluorescence detection kit CellTiter-Glo ® Luminescent Cell Viability Assay | Promega G7573 |
| GAS-Ad-BD medium | K2 Oncology, K2O-CML-01801 |
| BEZ235 | MCE |
| Gemcitabine | |
| Cisplatin | MCE |
| 5-fluorouracil | MCE |
| Matrigel | BD 356231 |

Experiment Method (1) Preparation of the Compound Plate

The compounds were dissolved in DMSO, then diluted 3-fold to obtain stock solutions (1000×) with 10-concentration gradients, and diluted 100-fold using GAS-Ad-BD medium to obtain working solutions (10×).

(2) Experimental Procedures

After tumor organoids could be passaged, matrigel was melted at 4° C. for later use. Cultured tumor organoids were collected using a Pasteur dropper and added with pancreatin to form a single cell suspension. After cell counting, the cell concentration was adjusted to $8\times10^4$ cell/mL by using GAS-Ad-BD medium, and 2 mL of the cell suspension was placed on ice for later use. A matrigel mixed solution was prepared by mixing the cell suspension and the matrigel and then placed on ice for later use, 50 uL of the mixed solution was added to a 96-well plate, incubated at 37° C. for 30 min and added with GAS-Ad-BD medium, and after 2 days of incubation in a 37° C. cell incubator, the formation and growth of tumor organoids were observed.

After the formation and growth of the tumor organoids were observed, 10 μL of working solutions (10×) with 10-concentration gradients prepared on the same day were sequentially added. The solutions were incubated at 37° C. for 96 h with 5% carbon dioxide. The starting concentrations of each compound were as follows: compound 29 at 10 μM, gemcitabine at 40 μM, cisplatin at 60 μM, and 5-fluorouracil at 30 μM. A solvent negative control group (DMSO, 100% survival) and a positive control group (2.5 μM BEZ235, 0% survival) were set.

After the cultivation was completed, 70 μL of CellTiter-Glo® solution was added, and the fluorescence value was determined after the operation was performed according to the specification.

(3) Data Processing

The corresponding compound concentration at 50% survival was calculated by using GraphPad Prism 5 software, that is the $IC_{50}$ value (absolute $IC_{50}$ value) for the compounds on these cells.

Test results:

TABLE 7

Inhibitory Activity of Compounds of the Present Invention Against KOBD-002 Distal Cholangiocarcinoma Organoids

| Test samples | $IC_{50}$(μM) |
|---|---|
| Compound 29 | 1.27 |
| Gemcitabine | 17.97 |
| Cisplatin | 18.77 |
| 5-fluorouracil | >30 |

It can be seen from the experimental results in Table 7 that the compounds of the present invention have a good inhibitory activity against KOBD-002 distal cholangiocarcinoma organoids, and are superior to gemcitabine, cisplatin and 5-fluorouracil, which indicates that the compounds have good clinical application potential in treating cholangiocarcinoma, and especially distal cholangiocarcinoma.

Experimental Example 4: In Vivo Efficacy Test of Compounds of the Present Invention on HuPrime® Human Cholangiocarcinoma CC6204 Subcutaneous Xenograft Tumor Model Test samples: the compounds of the present invention, which have structures shown in Table 1 and are prepared as described in the embodiments of WO2018108079A1; gemcitabine hydrochloride, commercially available.

The source of tumor mass: CC6204 was a HuPrime® xenograft model established by a female cholangiocarcinoma patient. The pathological diagnosis was intrahepatic cholangiocarcinoma, with FGFR2-BICC1 fusion aberration.

Animals: Balb/c nude female mice at 5-6 weeks (weeks of age at time of mice inoculation).

Test Method:

(1) Construction and Grouping of Tumor-Bearing Mice

Tumor tissues were collected from tumor-bearing mice of HuPrime® cholangiocarcinoma xenograft model CC6204, cut into tumor masses of a diameter of 2-3 mm and then subcutaneously inoculated into the right anterior scapula of the Balb/c nude mice, and the mice were grouped and administered when an average volume of tumors reached 133 $mm^3$. Grouping method: animals were weighed before administration and tumor volumes were measured. Grouping was designed in blocks according to the tumor volume, with 6 mice per group.

(2) Administration Regimen

TABLE 8

Administration regimen

| Group | Vehicle | Dosage (mg/kg) | Dosing volume (mL/kg) | Route of administration | Frequency of administration | Administration period |
|---|---|---|---|---|---|---|
| Vehicle control | 0.5% (v/v) MC containing 0.5% (v/v) Tween 80 | 0 | 10 | Oral intragastric administration | Qd | 68 days |
| Compound 29 | 0.5% (w/v) MC | 15 | 10 | Oral intragastric administration | Qd | 68 days |
| Gemcitabine hydrochloride | Normal saline | 120 | 10 | Intraperitoneal | QW [a] | 68 days |

Note:
[a] gemcitabine hydrochloride was administered once a week for a total of 10.

(3) Experimental Observation Index

Animals were monitored daily for health and mortality, body weight and tumor volume were measured twice a week, and samples were collected after the last administration. The therapeutic effect of tumor volume was evaluated by TGI %, wherein the relative tumor inhibition rate TGI (%): TGI=1−T/C (%). T/C % is the relative tumor proliferation rate, i.e., the percentage of the relative tumor volume in the treatment and control groups at a given time point. T and C are relative tumor volumes (RTVs) of the treatment and control groups at a given time point, respectively.

The calculation formula is as follows: T/C %=$T_{RTV}$/$C_{RTV}$×100% ($T_{RTV}$: mean RTV for treatment group; $C_{RTV}$: mean RTV for vehicle control group; RTV=$V_t/V_0$, wherein $V_0$ is the tumor volume of the animal at the time of grouping, and $V_t$ is the tumor volume of the animal after treatment). The drug is considered to be effective according to the National Institute of Health (NIH) Guidelines that TGI is ≥58%.

Test Results:

TABLE 9

Effect of Compounds of the Present Invention on Tumor Growth in Mice of HuPrime ® Human Cholangiocarcinoma CC6204 subcutaneous xenograft tumor model

| Group | Number of animals | Tumor volume [a] ($mm^3$) | TGI (%)[b] | P[c] |
|---|---|---|---|---|
| Vehicle control | 6 | 696.52 | — | — |
| Compound 29 | 6 | 147.8 | 80 | <0.001 |

TABLE 9-continued

Effect of Compounds of the Present Invention on Tumor Growth in Mice of HuPrime ® Human Cholangiocarcinoma CC6204 subcutaneous xenograft tumor model

| Group | Number of animals | Tumor volume [a] ($mm^3$) | TGI (%)[b] | P[c] |
|---|---|---|---|---|
| Gemcitabine hydrochloride | 6 | 397.22 | 43 | 0.973 |

Note:
[a] tumor volumes were statistic data for 21 days of administration.
[b]TGI: relative tumor inhibition rate, statistic data for 21 days of administration.
[c]P < 0.05 indicates that there was a statistical difference, P < 0.01 indicates that there was a significant statistical difference, and P < 0.001 indicates that there was an extremely significant statistical difference.

TABLE 10

Effect of Compounds of the Present Invention on Survival Rate of Mice of HuPrime ® Human Cholangiocarcinoma CC6204 subcutaneous xenograft tumor model

| Group | Number of animals | Number of surviving animals [a] | Survival rate (%) | P[b] |
|---|---|---|---|---|
| Vehicle control | 6 | 0 | 0 | — |
| Compound 29 | 6 | 6 | 100 | <0.001 |
| Gemcitabine hydrochloride | 6 | 1 | 16.7 | 0.467 |

Note:
[a] surviving animals were data statistics after the last administration (day 67).
[b]P < 0.05 indicates that there was a statistical difference, P < 0.01 indicates that there was a significant statistical difference, and P < 0.001 indicates that there was an extremely significant statistical difference.

The source of tumor mass: CC6639 was a HuPrime® xenograft model established by a male cholangiocarcinoma patient. The pathological diagnosis was intrahepatic cholangiocarcinoma, with no FGFR2 aberration.

Animals: Balb/c nude female mice at 4-5 weeks (weeks of age at time of mice inoculation).

Experiment Method (1) Construction and Grouping of Tumor-Bearing Mice

Tumor tissues were collected from tumor-bearing mice of HuPrime® cholangiocarcinoma xenograft model CC6639, cut into tumor masses of a diameter of 2-3 mm and then subcutaneously inoculated into the right anterior scapula of the Balb/c nude mice, and the mice were grouped and administered when an average volume of tumors reached 202 $mm^3$. Grouping method: animals were weighed before administration and tumor volumes were measured. Grouping was designed in blocks according to the tumor volume, with 5 mice per group.

(2) Administration Regimen Shown in Table 11

TABLE 11

Administration regimen

| Group | Vehicle | Dosage (mg/kg) | Dosing volume (mL/kg) | Route of administration | Frequency of administration | Administration period |
|---|---|---|---|---|---|---|
| Vehicle control | 0.5% (w/v)MC | 0 | 10 | Oral intragastric administration | Qd | 21 days |
| Compound 29 | 0.5% (w/v)MC | 15 | 10 | Oral intragastric administration | Qd | 21 days |

It can be seen from the experimental results in Table 9 and Table 10 that the compounds of the present invention have a remarkable inhibitory effect on HuPrime® human cholangiocarcinoma CC6204 subcutaneous xenograft tumor model, effectively prolong the life cycle of tumor-bearing animals, and are significantly superior to clinical standard treatment of gemcitabine, which indicates that the compounds of the present invention can be used in clinical treatment of intrahepatic cholangiocarcinoma tumors with FGFR2 aberration, and have good clinical application potential.

Experimental Example 5: In Vivo Efficacy Test of Compounds of the Present Invention on HuPrime® Human Cholangiocarcinoma CC6639 Subcutaneous Xenograft Tumor Model Test samples: the compounds of the present invention, which have structures shown in Table 1 and are prepared as described in the embodiments of WO2018108079A1.

(3) Experimental Observation Index

Animals were monitored daily for health and mortality, body weight and tumor volume were measured twice a week, and samples were collected after the last administration. The therapeutic effect of tumor volume was evaluated by TGI %, wherein the relative tumor inhibition rate TGI (%): TGI=1−T/C (%). T/C % is the relative tumor proliferation rate, i.e., the percentage of the relative tumor volume in the treatment and control groups at a given time point. T and C are relative tumor volumes (RTVs) of the treatment and control groups at a given time point, respectively. The calculation formula is as follows: T/C %=$T_{RTV}/C_{RTV}\times100\%$ ($T_{RTV}$: mean RTV for treatment group; $C_{RTV}$: mean RTV for vehicle control group; RTV=$V_t/V_0$, wherein $V_0$ is the tumor volume of the animal at the time of grouping, and $V_t$ is the tumor volume of the animal after treatment). The drug is considered to be effective according to the NIH Guidelines that TGI is ≥58%.

Test Results:

TABLE 12

Effect of Compound 29 of the present invention on tumor growth in mice of HuPrime ® human cholangiocarcinoma CC6639 subcutaneous xenograft tumor model

| Group | Number of animals | Tumor volume ($mm^3$) | TGI (%)[a] | P[b] |
|---|---|---|---|---|
| Vehicle control | 5 | 2195.88 | — | — |
| Compound 29 | 5 | 623.72 | 72 | 0.0045 |

Note:
[a]statistical data after the last administration;
TGI: relative tumor inhibition rate.
[b]P < 0.05 indicates that there was a statistical difference, P < 0.01 indicates that there was a significant statistical difference, and P < 0.001 indicates that there was an extremely significant statistical difference.

It can be seen from the experimental results in Table 12 that Compound 29 has a remarkable inhibitory effect on HuPrime® human cholangiocarcinoma CC6639 subcutaneous xenograft tumor model, which indicates that the compound can be used in clinical treatment of intrahepatic cholangiocarcinoma tumors with non-FGFR2 aberration and has good clinical application potential.

Experimental Example 6: In Vivo Efficacy Test of Compounds of the Present Invention on Human Perihilar Cholangiocarcinoma PDTX Subcutaneous Xenograft Tumor Model Test samples: the compounds of the present invention, which have structures shown in Table 1 and are prepared as described in the embodiments of WO2018108079A1.

The source of tumor mass: the human perihilar cholangiocarcinoma tumor sample was derived from a female patient.

Animals: NCG Male Mice at 5-8 Weeks.

Test Method:

(1) Construction and Grouping of Tumor-Bearing Mice

The tumor samples excised in the surgery were inoculated into mice as P0 generation and then passaged as P1 generation for drug efficacy evaluation. The tumor masses were inoculated into the right back of the mice, and the mice were grouped and administered when an average volume of tumors reached approximately 100 $mm^3$. Grouping method: animals were weighed before administration and tumor volumes were measured. Grouping was designed in blocks according to the tumor volume, with 6 mice per group.

(2) Administration According to Administration Regimen of Table 13

TABLE 13

Administration regimen

| Group | Vehicle | Dosage (mg/kg) | Dosing volume (mL/kg) | Route of administration | Frequency of administration | Administration period |
|---|---|---|---|---|---|---|
| Vehicle control | 0.5%(w/v)MC | 0 | 10 | Oral intragastric administration | Qd | 25 days |
| Compound 29 | 0.5%(w/v)MC | 15 | 10 | Oral intragastric administration | Qd | 25 days |
| Gemcitabine hydrochloride + Cisplatin | Normal saline | 30 + 3 | 10 + 10 | Intraperitoneal | BiW Qw | 25 days |

(3) Experimental Observation Index

Animals were monitored daily for health and mortality, body weight and tumor volume were measured twice a week, and samples were collected after the last administration. The therapeutic effect of tumor volume was evaluated by TGI %, wherein the relative tumor inhibition rate TGI (%): TGI=1−T/C (%). T/C % is the relative tumor proliferation rate, i.e., the percentage of the relative tumor volume in the treatment and control groups at a given time point. T and C are relative tumor volumes (RTVs) of the treatment and control groups at a given time point, respectively. The calculation formula is as follows: T/C %=$T_{RTV}/C_{RTV}\times 100\%$ ($T_{RTV}$: mean RTV for treatment group; $C_{RTV}$: mean RTV for vehicle control group; RTV=$V_t/V_0$, wherein $V_0$ is the tumor volume of the animal at the time of grouping, and $V_t$ is the tumor volume of the animal after treatment). The drug is considered to be effective according to the NIH Guidelines that TGI is ≥58%.

Test Results:

TABLE 14

Effect of Compound 29 of the Present Invention on Tumor Growth in Mice of HuPrime ® Human Cholangiocarcinoma CC6204 subcutaneous xenograft tumor model

| Group | Number of animals | Tumor volume [a] ($mm^3$) | TGI (%)[b] | P[c] |
|---|---|---|---|---|
| Vehicle control | 6 | 233.9 | — | — |
| Compound 29 | 6 | 70.9 | 70 | 0.0039 |
| Gemcitabine hydrochloride + Cisplatin | 6 | 157.3 | 35 | 0.247 |

Note:
[a] tumor volumes were statistical data for 21 days of administration;
[b]TGI: relative tumor inhibition rate, statistic data for 21 days of administration.
[c]P < 0.05 indicates that there was a statistical difference, P < 0.01 indicates that there was a significant statistical difference, and P < 0.001 indicates that there was an extremely significant statistical difference.

It can be seen from the experimental results in Table 14 that Compound 29 has a remarkable inhibitory effect on human perihilar cholangiocarcinoma PDTX subcutaneous xenograft tumor model, and is significantly superior to the clinical standard treatment of gemcitabine+cisplatin, which indicates that the compound of the present invention can be used in clinical treatment of perihilar cholangiocarcinoma tumors and has good clinical application potential.

The above description is only for the purpose of illustrating the preferred example of the present invention, and is not intended to limit the scope of the present invention. Any modifications, equivalents, improvements and the like made without departing from the spirit and principle of the present invention should be included in the protection scope of the present invention.

What is claimed is:

1. A method of treating a patient suffering from biliary tract cancer; comprising administering to the patient an effective amount of a compound of the following structure or a pharmaceutically acceptable salt, a stereoisomer and a crystal form thereof:

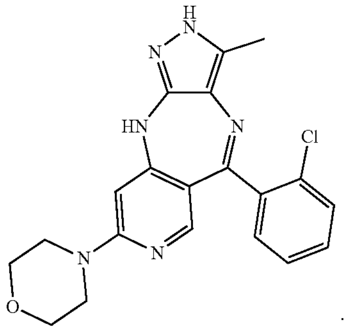 [SMILES: Cc1[nH]nc2c1N=C(c1ccccc1Cl)c1cnc(N3CCOCC3)cc1N2]

2. The method according to claim 1, wherein the biliary tract cancer is cholangiocarcinoma.

3. The method according to claim 2, wherein the cholangiocarcinoma is a cholangiocarcinoma with non-FGFR aberration.

4. The method according to claim 2, wherein the cholangiocarcinoma is a cholangiocarcinoma with FGFR aberration.

5. The method according to claim 4, wherein the cholangiocarcinoma is cholangiocarcinoma with any one of FGFR fusion, FGFR mutation and FGFR overexpression or any combination thereof.

6. The method according to claim 5, wherein the cholangiocarcinoma is cholangiocarcinoma with any one of FGFR2 fusion, FGFR2 and/or FGFR3 mutation and FGFR overexpression or any combination thereof.

7. The method according to claim 2, wherein the cholangiocarcinoma refers to drug-resistant cholangiocarcinoma that is positive for FGFR aberration but not responsive to an FGFR inhibitor, or drug-resistant cholangiocarcinoma after administration of an FGFR inhibitor.

8. The method according to claim 2, wherein the cholangiocarcinoma is any one of intrahepatic cholangiocarcinoma, perihilar cholangiocarcinoma and distal cholangiocarcinoma or any combination thereof.

9. The method according to claim 1, wherein the patient is further administered one or more second therapeutically active agents in addition to the compound as recited in claim 1, or the pharmaceutically acceptable salt, the stereoisomer or the crystal form thereof, wherein the one or more second therapeutically active agents are any one of an antimetabolite, a growth factor inhibitor, a mitotic inhibitor, an antitumor hormone, an alkylating agent, metallic platinum, a topoisomerase inhibitor, a hormonal agent, an immunomodulator, a tumor suppressor gene, a cancer vaccine and an immune checkpoint inhibitor or any combination thereof.

10. The method according to claim 9, wherein the compound as recited in claim 9, or the pharmaceutically acceptable salt, the stereoisomer or the crystal form thereof and the second therapeutically active agents are administered to a patient in need of treatment sequentially, simultaneously or in a combined formulation.

11. The method according to claim 10, wherein the patient is a mammal.

12. The method according to claim 11, wherein the patient is a human.

13. The method according to claim 1, wherein the biliary tract cancer is an FGFR-mediated cholangiocarcinoma.

14. The method according to claim 1, wherein the biliary tract cancer is cholangiocarcinoma mediated by any one of FGFR1, FGFR2 and FGFR3 or any combination thereof.

15. The method according to claim 2, wherein the cholangiocarcinoma is a cholangiocarcinoma with FGFR2 aberration and/or a cholangiocarcinoma with FGFR3 aberration.

* * * * *